United States Patent
Petkovic et al.

(10) Patent No.: US 8,361,777 B2
(45) Date of Patent: Jan. 29, 2013

(54) GENES FOR BIOSYNTHESIS OF TETRACYCLINE COMPOUNDS AND USES THEREOF

(75) Inventors: Hrvoje Petkovic, Ljubljana (SI); Peter Raspor, Ljubljana (SI); Urska Lesnik, Ljubljana (SI)

(73) Assignee: Univerza v Ljubljani, Ljubljana (SI)

( * ) Notice: Subject to any disclaimer, the term of this patent is extended or adjusted under 35 U.S.C. 154(b) by 523 days.

(21) Appl. No.: 12/536,622

(22) Filed: Aug. 6, 2009

(65) Prior Publication Data

US 2010/0035847 A1    Feb. 11, 2010

(30) Foreign Application Priority Data

Aug. 7, 2008    (EP) .................................... 08014141

(51) Int. Cl.
*C12N 1/20* (2006.01)
*C07H 21/04* (2006.01)
(52) U.S. Cl. .................................... 435/252.1; 536/23.1
(58) Field of Classification Search .................. None
See application file for complete search history.

(56) References Cited

PUBLICATIONS

Bijan Zakeri et al., "Chemical biology of tetracycline antibiotics[1]", Biochemistry and Cell Biology, vol. 86, No. 2, Apr. 2008, pp. 124-136 (XP002500431).

Tetsuo Nakano et al., "Identification and Cloning of the Gene Involved in the Final Step of Chlortetracycline Biosynthesis in *Streptomyces aureofaciens*", Bioscience Biotechnology and Biochemistry, vol. 68, No. 6, Jun. 2004, pp. 1345-1352 (XP002500432).
Wenjun Zhang et al., "Investigation of Early Tailoring Reactions in the Oxytetracycline Biosynthetic Pathway", Journal of Biological Chemistry, vol. 282, No. 35, Aug. 2007, pp. 25717-25725 (XP002500433).
Wenjun Zhang et al., "Engineered Biosynthesis of a Novel Amidated Polyketide, Using the Malonamyl-Specific Initiation Module from the Oxytetracycline Polyketide Synthase", Applied and Environmental Microbioloty, vol. 72, No. 4, Apr. 2006, pp. 2573-2580 (XP002500434).
Eung-Soo Kim et al., "Sequence of the oxytetracycline polyketide synthase-encoding *otc* genes from *Streptomyces rimosus*", Gene (Amsterdam), vol. 141, No. 1; 1994, pp. 141-142 (XP002500435).
Database UniProt [Online] 1-8, Mar. 1, 2001, "SubName: Full=Beta-ketoacyl synthase;" (XP002500437), retrieved from EBI accession No. Uniprot:Q9FAR5, Database accession No. Q9FAR5. The sequence has 77.3% identity with Seq ID No. 1. 3 pages.
S.A. Wood et al., "PCR screening reveals unexpected antibiotic biosynthetic potential in *Amycolatopsis* sp. strain UM16", Journal of Applied Microbiology, vol. 102, No. 1, Jan. 2007, pp. 245-253 (XP002500436).
Partial European Search Report from corresponding European Application No. EP 08 01 4141 dated Oct. 20, 2008.

*Primary Examiner* — Michele K Joike
(74) *Attorney, Agent, or Firm* — Renner, Otto, Boisselle & Sklar, LLP

(57) ABSTRACT

The invention relates to genetically engineered cells, and to proteins and genes useful in the production of tetracycline compounds, to methods of producing tetracycline compounds, and to tetracyclines thereby produced. The present invention is based on the cloning and heterologous expression of genes encoding the chelocardin biosynthetic pathway.

5 Claims, 4 Drawing Sheets

| SEQ ID NO: | Minimum set | | | | | | | | Oxygen | | | | homol. | | | | optional | | | | heterol. | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21/22/23/24 | 25 | 26 |
| Structure 1 | + | + | + | + | + | + | + | + | + | + | + | + | + | + | - | - | + | + | + | - | - | - | - |
| Structure 2 | + | + | + | + | + | + | + | + | + | + | + | + | + | - | - | - | + | + | - | - | - | - | - |
| Structure 3 | + | + | + | + | + | + | + | + | + | + | + | + | + | + | - | - | + | + | - | + | - | - | - |
| Structure 4 | + | + | + | + | + | + | + | + | + | + | + | + | + | + | - | - | + | + | - | - | + | - | - |
| Structure 5 | + | + | + | + | + | + | + | + | + | + | + | - | + | + | - | - | + | + | - | - | + | - | - |
| Structure 6 | + | + | + | + | + | + | + | + | + | + | + | + | + | + | - | - | + | + | - | - | - | - | - |
| Structure 7 | + | + | + | + | + | + | + | + | + | + | + | + | - | + | - | - | + | + | - | - | - | + | - |
| Structure 8 | + | + | + | + | + | + | + | + | + | + | + | + | + | + | - | - | + | + | - | - | - | - | - |
| Structure 9 | + | + | + | + | + | + | + | + | + | + | + | + | + | + | - | - | + | + | - | - | - | - | + |
| Structure 10 | + | + | + | + | + | + | + | + | - | - | - | - | - | - | - | - | - | - | - | - | - | - | - |

Figure 6

```
                        SEQUENCE LISTING

<160> NUMBER OF SEQ ID NOS: 45

<210> SEQ ID NO 1
<211> LENGTH: 432
<212> TYPE: PRT
<213> ORGANISM: Amycolatopsis sp.

<400> SEQUENCE: 1

Val Thr Gly Pro Ser Asp Ala His Arg Val Val Ile Thr Gly Ile Gly
1               5                   10                  15

Val Val Ala Pro Gly Asp Arg Gly Thr Lys Gln Phe Trp Glu Leu Ile
            20                  25                  30

Thr Ala Gly Arg Thr Ala Thr Arg Pro Ile Ser Leu Phe Asp Ala Ser
        35                  40                  45

Ser Phe Arg Ser Arg Val Ala Ala Glu Cys Asn Phe Asp Pro Ile Ala
    50                  55                  60

Ala Gly Leu Ser Gln Arg Gln Ile Arg Lys Trp Asp Arg Thr Thr Gln
65                  70                  75                  80

Phe Cys Val Val Ala Ala Arg Glu Ala Val Ala Asp Ser Gly Met Leu
                85                  90                  95

Gly Glu Gln Asp Pro Leu Arg Thr Gly Val Ala Ile Gly Thr Ala Cys
            100                 105                 110

Gly Met Thr Gln Ser Leu Asp Arg Glu Tyr Ala Val Val Ser Asp Glu
        115                 120                 125

Gly Ser Ser Trp Leu Val Asp Pro Asp Tyr Gly Val Pro Gln Leu Tyr
    130                 135                 140

Asp Tyr Phe Leu Pro Ser Ser Met Ala Thr Glu Ile Ala Trp Leu Val
145                 150                 155                 160

Glu Ala Glu Gly Pro Val Gly Leu Val Ser Thr Gly Cys Thr Ser Gly
                165                 170                 175

Val Asp Val Ile Gly His Ala Ala Asp Leu Ile Arg Asp Gly Glu Ala
            180                 185                 190

Asp Ile Met Val Ala Gly Ala Ser Glu Ala Pro Ile Ser Pro Ile Thr
        195                 200                 205

Val Ala Cys Phe Asp Ala Ile Lys Ala Thr Thr Ala Arg Asn His Glu
    210                 215                 220

Pro Glu Ser Ala Ser Arg Pro Phe Asp Gln Thr Arg Ser Gly Phe Val
225                 230                 235                 240

Leu Gly Glu Gly Ala Ala Val Phe Val Leu Glu Glu Leu Arg His Ala
                245                 250                 255

Lys Arg Arg Gly Ala His Ile Tyr Ala Glu Ile Val Gly Tyr Ala Ser
            260                 265                 270

Arg Cys Asn Ala Tyr Ser Met Thr Gly Leu Arg Pro Asp Gly Arg Glu
```

-continued

```
                    275                 280                 285
Met Ala Asp Ala Ile Asp Gly Ala Leu Asn Gln Ala Arg Ile Asp Pro
    290                 295                 300

Ser Arg Ile Gly Tyr Val Asn Ala His Gly Ser Ser Thr Arg Gln Asn
305                 310                 315                 320

Asp Arg His Glu Thr Ala Ala Ile Lys Thr Ser Leu Gly Ala His Ala
                325                 330                 335

Tyr Gln Val Pro Val Ser Ser Ile Lys Ser Met Val Gly His Ser Leu
                340                 345                 350

Gly Ala Ile Gly Ser Leu Glu Val Ala Ala Cys Ala Leu Thr Ile Glu
                355                 360                 365

His Ser Val Ile Pro Pro Thr Ala Asn Leu His Val Pro Asp Pro Glu
                370                 375                 380

Cys Asp Leu Asp Tyr Val Pro Leu Val Ala Arg Glu Gln Glu Val Asp
385                 390                 395                 400

Val Val Leu Ser Val Ala Ser Gly Phe Gly Gly Phe Gln Ser Ala Ile
                405                 410                 415

Leu Leu Thr Gly Pro Asp Gly Arg Thr Gly Lys Arg Val Thr Gln Arg
                420                 425                 430

<210> SEQ ID NO 2
<211> LENGTH: 409
<212> TYPE: PRT
<213> ORGANISM: Amycolatopsis sp.

<400> SEQUENCE: 2

Val Pro Gly Arg Ser Thr Val Arg Pro Val Thr Gly Leu Gly Val
1               5                   10                  15

Ile Ala Pro Asn Gly Met Gly Thr Glu Ala Tyr Trp Ala Ala Thr Leu
                20                  25                  30

Arg Gly Asp Ser Gly Leu Arg Arg Ile Thr Arg Phe Asp Pro Asp Gly
            35                  40                  45

Tyr Pro Ala Arg Ile Ala Gly Glu Val Ser Phe Asp Pro Ala Gly Arg
        50                  55                  60

Leu Pro Asp Arg Leu Leu Pro Gln Thr Asp His Met Thr Arg Leu Ala
65                  70                  75                  80

Leu Ile Ala Ala Glu Glu Ala Leu Ala Asp Ala Gly Ala Asp Pro Arg
                85                  90                  95

Asn Leu Pro Asp Tyr Ala Thr Gly Val Met Thr Ala Ala Ser Gly Gly
                100                 105                 110

Gly Phe Glu Phe Gly Gln Arg Glu Leu Gln Glu Leu Trp Ser Lys Gly
            115                 120                 125

Gly Ser Tyr Val Ser Ala Tyr Gln Ser Phe Ala Trp Phe Tyr Pro Val
        130                 135                 140

Asn Thr Gly Gln Ile Ser Ile Arg His Gly Met Arg Gly Ser Ser Gly
145                 150                 155                 160

Thr Leu Val Ser Glu Gln Ala Gly Gly Leu Asp Ala Val Ala Lys Ala
                165                 170                 175

Arg Arg His Val Arg Asp Gly Thr Pro Leu Met Val Thr Gly Gly Ile
                180                 185                 190

Asp Gly Ser Leu Cys Pro Trp Ser Trp Leu Cys Met Leu Arg Ser Gly
            195                 200                 205

Arg Leu Ser Thr Ala Ser Asp Pro Gln Arg Ala Tyr Leu Pro Phe Asp
        210                 215                 220

Thr Glu Ala Ser Gly Met Val Pro Gly Glu Gly Gly Ala Leu Leu Val
```

```
             225                 230                 235                 240
    Ile Glu Asp Pro Ala Ala Gln Arg Arg Gly Val Asp Arg Ile Tyr
                    245                 250                 255

Gly Gln Ile Ala Gly Tyr Cys Ala Thr Phe Asp Pro Gly Pro Gly Ser
                    260                 265                 270

Arg Arg Pro Pro Gly Leu Arg Arg Ala Val Glu Gln Ala Leu Ala Glu
                    275                 280                 285

Ala Arg Leu His Pro Ser Glu Val Asp Val Val Phe Ala Asp Ala Ala
                290                 295                 300

Gly Leu Pro Asp Leu Asp Arg Ala Glu Ile Glu Val Leu Val Arg Ile
    305                 310                 315                 320

Phe Gly Ala Arg Ala Val Pro Val Thr Ala Pro Lys Thr Met Thr Gly
                    325                 330                 335

Arg Leu Leu Ala Gly Gly Ser Ser Leu Asp Leu Ala Thr Ala Leu Leu
                    340                 345                 350

Ser Leu Arg Asp Lys Val Ile Pro Pro Thr Val His Ile Gly Lys Phe
                    355                 360                 365

Gly Tyr Arg Asp Glu Ile Asp Leu Val Arg Asp Ser Pro Arg Gln Ala
                370                 375                 380

Pro Leu Ser Thr Ala Leu Val Leu Ala Arg Gly Tyr Gly Gly Phe Asn
    385                 390                 395                 400

Ser Ala Met Val Leu Arg Gly Ala Thr
                    405

<210> SEQ ID NO 3
<211> LENGTH: 88
<212> TYPE: PRT
<213> ORGANISM: Amycolatopsis sp.

<400> SEQUENCE: 3

Met Ala Glu Phe Thr Ile Ala Glu Leu Val Arg Leu Leu Arg Glu Cys
1               5                   10                  15

Ala Gly Glu Glu Glu Gly Val Asp Leu Asp Gly Glu Val Gly Asp Leu
                20                  25                  30

Pro Phe Asp Glu Leu Gly Tyr Asp Ser Leu Ala Leu Phe Asn Thr Ile
            35                  40                  45

Gly Arg Ile Glu Arg Glu Tyr Thr Val Asp Leu Pro Glu Asp Val Val
        50                  55                  60

Trp Gln Ala Thr Thr Pro Gly Ala Leu Val Asp Leu Val Asn Ser Ser
65                  70                  75                  80

Arg Thr Ser Pro Ala Ala Ala Asp
                85

<210> SEQ ID NO 4
<211> LENGTH: 302
<212> TYPE: PRT
<213> ORGANISM: Amycolatopsis sp.

<400> SEQUENCE: 4

Met Ser His Pro Glu Ala Glu Gln Thr Gln Ala Ser Ile Val Val Asp
1               5                   10                  15

Ala Pro Ala Glu Ile Thr Tyr Ala Met Leu Val Asp Val Ala Asn Trp
                20                  25                  30

Pro Leu Leu Tyr Pro Trp Ile Ala His Thr Glu Phe Val Glu Arg Ala
            35                  40                  45

Pro Thr Glu Asp Leu Val Gln Phe Trp Ala Val Asn Pro Leu Gly Arg
        50                  55                  60
```

```
Ile Arg Ile Trp Thr Ser Arg Arg Tyr Leu Asp Ala Ser Ala Leu Arg
 65                  70                  75                  80

Met Asp Ile Glu Gln Gln Gly Ser Val Gly Pro Ile Thr Gly Leu Thr
                 85                  90                  95

Gly Ser Trp Thr Phe Lys Pro Leu Pro Gly Asp Arg Cys Leu Val Glu
            100                 105                 110

Ser Arg His Ala Phe His Ala Ala Thr Pro Glu Asp Arg Ala Ala Gly
        115                 120                 125

Val Thr Glu Leu Asn Arg His Gly Lys Leu Gln Met Glu Thr Leu Lys
    130                 135                 140

Ser Arg Val Glu Asn Arg Thr Arg Leu Ala Glu Leu Thr Trp Ser Phe
145                 150                 155                 160

Glu Asp Ser Leu Val Ile Glu Ser Glu Leu Gly Gln Val Tyr Arg Ala
                165                 170                 175

Leu Arg Asp Val Gly Ser Trp Pro Ala His Leu Pro Cys Leu Thr Ala
            180                 185                 190

Leu Glu Val Thr Glu Asp Glu Asn Asp Val Gln Phe Tyr Asp Val Arg
        195                 200                 205

Thr Gln Asp Ala Asp Glu Pro Ser Arg Phe Val Arg Ile Cys Leu Pro
    210                 215                 220

Asp Lys Gly Ile Ala Tyr Lys Gln Leu Thr Val Thr Ala Pro Val Asp
225                 230                 235                 240

Leu His Leu Gly Arg Trp Thr Leu Thr Glu Thr Pro Ala Gly Val Ala
                245                 250                 255

Val Thr Ser Ala His Thr Val Leu Val Asn Pro Ser Ala Ala Glu Gln
            260                 265                 270

Leu Pro Glu Leu Arg Asp Arg Leu His Lys Thr Ser Ser Ala Asp Ser
        275                 280                 285

Leu Ala Glu Leu Gln Leu Val Lys Arg Leu Ala Glu Thr Arg
    290                 295                 300

<210> SEQ ID NO 5
<211> LENGTH: 315
<212> TYPE: PRT
<213> ORGANISM: Amycolatopsis sp.

<400> SEQUENCE: 5

Met Pro Ala Ala Ala Gln Gln His Thr Glu His Arg Ile Asp Ile Asp
 1               5                  10                  15

Ala Pro Ala Gly Leu Val Tyr Arg Ile Ile Ala Asp Ala Thr Glu Trp
                20                  25                  30

Pro Arg His Phe Thr Pro Thr Val His Val Asp Gln Ser Glu Leu Asp
            35                  40                  45

Gly His Thr Glu Arg Leu His Ile Trp Ala Asn Ala Asn Gly Gln Leu
        50                  55                  60

Lys Ser Trp Thr Ser Leu Arg Glu Leu Asp Glu Arg Ala Gly Arg Ile
 65                  70                  75                  80

Arg Phe Arg Gln Glu Val Ser Ala Pro Val Ala Ser Met Ser Gly
                 85                  90                  95

Glu Trp Ile Val Ser Glu Arg Val Ala Glu Arg Thr Thr Leu Val Leu
            100                 105                 110

Thr His Asp Phe Ala Ala Val Asp Asp Pro Ala Gly Val Glu Trp
        115                 120                 125

Ile Thr Lys Ala Thr Asn Gly Asn Ser Asp Thr Glu Leu Ala Asn Ile
    130                 135                 140
```

```
Lys Ala Leu Ala Glu Arg Trp Glu Arg Met Asp Arg Leu Ala Phe Asp
145                 150                 155                 160

Phe Glu Asp Ser Val Leu Val Arg Ala Pro Lys Glu Arg Ala Tyr His
            165                 170                 175

Phe Leu Asp Arg Val Asp Leu Trp Pro Asp Arg Leu Pro His Val Ala
        180                 185                 190

Arg Leu Glu Leu Arg Glu Asp Val Pro Gly Val Gln His Met Ser Met
    195                 200                 205

Asp Thr Lys Ala Lys Asp Gly Ser Thr His Thr Val Ser Val Arg
    210                 215                 220

Val Cys Phe Pro Glu Ala Arg Ile Val Tyr Lys Gln Leu Val Pro Pro
225                 230                 235                 240

Ala Leu Leu Thr Thr His Thr Gly Val Trp Thr Phe Glu Asp Thr Ala
            245                 250                 255

Asp Gly Val Leu Val Thr Ser Ala His Thr Val Val Leu Asn Glu Ala
        260                 265                 270

Asn Ile Gly Thr Val Pro Gly Pro Ala Ala Thr Val Glu Ser Thr Arg
    275                 280                 285

Asp Phe Val Arg Asn Ala Ile Ser Gly Asn Ser Gln Ala Thr Leu Arg
290                 295                 300

His Ala Lys Ala Phe Ala Glu Ala Thr Asp Ala
305                 310                 315

<210> SEQ ID NO 6
<211> LENGTH: 150
<212> TYPE: PRT
<213> ORGANISM: Amycolatopsis sp.

<400> SEQUENCE: 6

Met Ser Gln Ala Val Gln Ala Val Gly Ser Thr Glu Asp Ile Ala Leu
1               5                   10                  15

Tyr Val Glu Val Gln Gln Phe Tyr Gly Arg Gln Met Arg Tyr Leu Asp
            20                  25                  30

Glu Gly Arg Val Gln Glu Trp Ala Lys Thr Phe Thr Glu Asp Gly Met
        35                  40                  45

Phe Ala Ala Asn Ala His Pro Glu Pro Ala Arg Gly Arg Thr Ala Ile
    50                  55                  60

Glu Ala Gly Ala Leu Glu Ala Ala Thr Arg Leu Ala Glu Gln Gly Ile
65                  70                  75                  80

Gln Arg Arg His Trp Leu Gly Met Val Gln Val Asp Pro Gln Pro Asp
                85                  90                  95

Gly Ser Ile Val Ala Lys Ser Tyr Ala Val Ile Ile Gly Thr Pro Leu
            100                 105                 110

Gly Gly Lys Ala Ala Val Asp Leu Ser Cys Asp Cys Val Asp Val Leu
        115                 120                 125

Val Arg Glu Gly Gly Ala Leu Leu Val Arg Glu Arg Gln Val Tyr Arg
    130                 135                 140

Asp Asp Leu Pro Arg Asn
145                 150

<210> SEQ ID NO 7
<211> LENGTH: 452
<212> TYPE: PRT
<213> ORGANISM: Amycolatopsis sp.

<400> SEQUENCE: 7
```

-continued

```
Val Ala Cys Leu Gln Phe Thr Ser Gly Thr Thr Gly Ala Ala Lys Ala
1               5                   10                  15

Val Arg Leu Ser His Arg Asn Ile Thr Val Asn Ala Ala Gln Ser Gly
            20                  25                  30

His Ala His Gly Ile Thr Pro Ser Ser Val Leu Phe Asn Tyr Leu Pro
        35                  40                  45

Thr Phe His Leu Met His Leu Thr Met Ala Val Thr Phe Ala Ala Thr
    50                  55                  60

Leu Val Leu His Val Gly Asp Val Ala Gln Ala Val Asp Ala Ala
65                  70                  75                  80

Asp Asn Glu Lys Ala Thr His Phe Tyr Ser Leu Pro Met Arg Leu Ser
                85                  90                  95

Arg Leu Ala Val His Pro Arg Leu Ser Thr Leu Ala Ala Asp Ala Leu
            100                 105                 110

Gln Val Ile Leu Cys Gly Gly Ser Ala Leu Pro Leu Pro Ser Thr Arg
        115                 120                 125

Ala Leu Thr Gly Cys Phe Gly Val Pro Val Val Gln Gly Tyr Gly Leu
    130                 135                 140

Gln Glu Thr Ser Pro Ser Thr His Phe Asp Ser Leu Ser Cys Pro Lys
145                 150                 155                 160

Thr Gly Ser Ser Gly Arg Pro Val Ala Gly Thr Gly Cys Arg Ile Val
                165                 170                 175

Asp Val Asp Ser Arg Ala Val Leu Pro Val Gly Glu Lys Gly Glu Ile
            180                 185                 190

Gln Val Arg Gly Pro Gln Leu Met Leu Gly Tyr Leu Gly Arg Glu Pro
        195                 200                 205

Gly Gln Asp Val Asp Pro Asp Gly Trp Phe Ser Thr Gly Asp Val Gly
210                 215                 220

Tyr Val Asp Ala Glu Gly Val Leu Phe Val Val Asp Arg Ile Lys Asp
225                 230                 235                 240

Val Phe Lys Cys Asp Asn Trp Leu Val Ser Pro Thr Glu Ile Glu Arg
                245                 250                 255

Val Val Leu Ser His Pro Glu Val Ala Asp Cys Val Val Leu Asp Tyr
            260                 265                 270

Pro Asp Asp Phe Ser Gly Ser Val Ala Tyr Gly Leu Val Val Pro Lys
        275                 280                 285

Gly Ala Gly Leu Asn Pro Ala Gln Leu Ala Glu Phe Val Ala Glu Arg
290                 295                 300

Leu Pro Tyr Tyr Ala His Leu Arg His Val Glu Leu Thr Asp Arg Ile
305                 310                 315                 320

Pro Arg Ser Pro Asn Gly Lys Leu Gln Arg Arg Ala Leu Arg Glu Gln
                325                 330                 335

Ile His Ala Arg Asn Ala Asp Gly Ala Ser Glu Ile Ala Arg Gln Asn
            340                 345                 350

Arg Ser Lys Thr Val Phe Thr Phe Ile Asn Arg Phe Thr Val Thr Gly
        355                 360                 365

Asp Ala Thr Glu Phe Arg Arg Leu Leu Gly Gln Ile Thr Ala His Met
370                 375                 380

Thr Ala Gln Pro Gly Phe Arg Ser His Arg Leu Tyr Gln Ser Ala Arg
385                 390                 395                 400

Asp Glu Ala Val Phe Thr Glu Ile Ala Glu Trp Asp Ser Ala Glu Asp
                405                 410                 415

His Gln Arg Ala Thr Ala Gly Lys Gly Phe Arg Glu Pro Val Gly Glu
            420                 425                 430
```

Ala Met Lys His Ala Thr Ala Glu Pro Ala Pro Phe Val Leu Arg Ala
        435                 440                 445

Glu His Gly Ala
    450

<210> SEQ ID NO 8
<211> LENGTH: 262
<212> TYPE: PRT
<213> ORGANISM: Amycolatopsis sp.

<400> SEQUENCE: 8

Met Arg Ser Thr Glu Glu Pro Arg Val Ala Leu Val Thr Gly Ala Thr
1               5                   10                  15

Ser Gly Ile Gly Leu Ala Val Thr Lys Ala Leu Ala Ala Arg Gly Leu
            20                  25                  30

Arg Val Phe Ile Cys Ala Arg Asn Arg Glu Asn Val Val Ser Thr Val
        35                  40                  45

Lys Glu Leu Arg Ala Gln Gly Leu Asp Val Asp Gly Gln Ala Gly Asp
    50                  55                  60

Val Arg Ser Val Ala Ala Val Arg Glu Val Val Glu Ser Ala Val Asn
65                  70                  75                  80

Arg Phe Gly Thr Ile Ser Val Leu Val Asn Asn Ala Gly Arg Ser Gly
                85                  90                  95

Gly Gly Ile Thr Ala Lys Ile Thr Asp Glu Leu Trp Gln Asp Val Ile
            100                 105                 110

Asp Thr Asn Leu Asn Ser Val Phe Thr Val Thr Arg Glu Val Leu Thr
        115                 120                 125

Thr Gly Gly Leu Asp Gly Ala Asp Gly Gly Arg Ile Ile Asn Ile Ala
    130                 135                 140

Ser Thr Gly Gly Lys Gln Gly Val Pro Leu Gly Ala Pro Tyr Ser Ala
145                 150                 155                 160

Ala Lys Ser Gly Val Ile Gly Phe Thr Lys Ala Leu Gly Lys Glu Leu
                165                 170                 175

Ala Lys Thr Gly Val Thr Val Asn Ala Val Cys Pro Gly Tyr Val Glu
            180                 185                 190

Thr Pro Met Ala Val Arg Val Arg Gln Ala Tyr Ala Ser Thr Trp Asp
        195                 200                 205

Thr Thr Asp Glu Asn Val Leu Ala Arg Phe Asn Asp Lys Ile Pro Leu
    210                 215                 220

Gly Arg Tyr Cys Thr Pro Glu Glu Val Ala Gly Met Val Asp Tyr Leu
225                 230                 235                 240

Val Ala Asp Thr Ala Ala Ser Val Thr Ala Gln Ala Ile Asn Val Cys
                245                 250                 255

Gly Gly Leu Gly Asn Tyr
            260

<210> SEQ ID NO 9
<211> LENGTH: 404
<212> TYPE: PRT
<213> ORGANISM: Amycolatopsis sp.

<400> SEQUENCE: 9

Met Thr Asp Ile Arg Thr Asp Phe Cys Val Gly Gly Gly Pro Ala
1               5                   10                  15

Gly Leu Thr Leu Ala Leu Leu Leu Ala Arg Ser Gly Val Arg Val Val
            20                  25                  30

```
Val Val Glu Arg Ser Arg Ser Phe Asp Arg Glu Tyr Arg Gly Glu Ile
         35                  40                  45

Leu Gln Pro Gly Gly Gln Ala Leu Leu Ala Glu Leu Gly Val Leu Thr
 50                  55                  60

Pro Ala Arg Glu His Gly Ala His Glu His His Arg Phe Leu Leu Glu
 65                  70                  75                  80

Glu His Gly Lys Val Leu Ile Asn Gly Asp Tyr Arg Arg Leu Pro Gly
                 85                  90                  95

Pro Phe Asn Cys Leu Leu Ser Ile Pro Gln Arg His Leu Leu Arg Glu
            100                 105                 110

Leu Leu Ala Gln Cys His Glu His Ala Gly Phe Gln Tyr Leu Ser Gly
        115                 120                 125

Thr Lys Val Thr Gly Leu Val Glu Asp Gly Arg Val Arg Gly Val
130                 135                 140

Val Cys Gly Asp Asp Gln Val Val Leu Ala His Cys Val Ile Gly Ala
145                 150                 155                 160

Asp Gly Arg Tyr Ser Lys Val Arg Gln Leu Ala Gly Ile Pro Ala Asp
                165                 170                 175

Arg Val Glu Gly Phe Arg Gln Asp Val Leu Trp Phe Lys Leu Ser Ala
            180                 185                 190

Asp Gly Glu Leu Pro Ser Glu Val Arg Val Phe Arg Ala Gly Gly Asn
        195                 200                 205

Pro Val Leu Ala Tyr Thr Ser Val Arg Asp Arg Val Gln Phe Gly Trp
210                 215                 220

Thr Leu Pro His Lys Gly Tyr Gln Leu Leu Ala Gln Gln Gly Leu Ala
225                 230                 235                 240

His Ile Lys Glu Gln Leu Arg Ala Ala Val Pro Gly Tyr Ala Asp Arg
                245                 250                 255

Ile Asp Glu Glu Ile Thr Ser Phe Arg Asp Leu Ser Leu Leu Asp Val
            260                 265                 270

Phe Ser Gly Gly Ala Arg Gln Trp Val Arg Asp Gly Leu Leu Leu Ile
        275                 280                 285

Gly Asp Ser Ala His Thr His Gly Pro Ile Gly Ala Gln Gly Ile Asn
290                 295                 300

Leu Ala Ile Gln Asp Ala Val Ala Ala His Pro Leu Leu Glu Ser
305                 310                 315                 320

Leu Arg Ala Asn Asp Ser Ser Gly Ala Met Leu Gly Arg Phe Val Thr
                325                 330                 335

Gly Arg Lys Arg Asp Ile Asp Arg Met Asn Arg Ile Gln Ala Val Gln
            340                 345                 350

Gly Lys Ala Met Leu Ser Ala Gly Arg Val Ser Ser Val Val Arg Pro
        355                 360                 365

Arg Leu Ala Met Val Val Ala Arg Thr Pro Ile Tyr Arg Ala Met Leu
370                 375                 380

Arg Gln Ile Ala Phe Gly Asn Thr Gly Ile Arg Ile Arg Ala Glu Leu
385                 390                 395                 400

Phe Ala Arg Arg

<210> SEQ ID NO 10
<211> LENGTH: 430
<212> TYPE: PRT
<213> ORGANISM: Amycolatopsis sp.

<400> SEQUENCE: 10

Met Pro Arg Arg Ser Pro Arg Arg Pro Met Pro Glu Asp Ser Gly Glu
```

-continued

```
 1               5                  10                 15
Glu Pro Glu Val Leu Val Ala Gly Ala Gly Pro Val Gly Leu Thr Ala
                20                  25                 30
Ala His Glu Leu Ala Arg Arg Gly Val Arg Val Arg Leu Val Asp Arg
                35                  40                 45
Ser Ala Gly Pro Ala Thr Thr Ser Arg Ala Leu Ala Thr His Ala Arg
 50                 55                 60
Thr Leu Glu Ile Trp His Gln Met Gly Leu Leu Gly Glu Leu Leu Pro
 65                 70                 75                 80
Arg Gly Arg Arg Val Glu His Phe Thr Leu His Leu Lys Gly Lys Thr
                85                  90                 95
Leu Met Cys Phe Asp Thr Asn Tyr Asp Thr Met Pro Thr Arg Phe Pro
                100                 105                110
Phe Ser Leu Met Val Asp Gln Val Val Thr Glu Glu Val Leu Arg Arg
                115                 120                125
Gln Val Arg Ala Leu Gly Val Thr Val Glu Trp Gly Val Glu Leu Thr
                130                 135                140
Trp Phe Asp Gln Glu Pro Asp Gly Val Leu Ala Glu Leu Arg His Ala
145                 150                 155                160
Asp Gly Thr Val Glu Gln Val Thr Ala Ala Trp Leu Val Gly Ala Asp
                165                 170                175
Gly Ala Arg Ser Thr Val Arg Lys Arg Leu Asp Leu Arg Leu Gln Gly
                180                 185                190
Asp Ser Thr Gln Thr Trp Leu Asn Ala Asp Val Val Leu Asp Thr Asp
                195                 200                205
Leu Leu Pro Val Gly Pro His Val Val Leu Asp Pro Ala Ala Gln Leu
                210                 215                220
Gln Pro Leu Asp Pro Val Arg Leu Asp Leu Pro Arg Ser Ala Glu Pro
225                 230                 235                240
Arg Thr His Val Arg His His Gly Val Leu Glu Arg Arg Leu Leu
                245                 250                255
Gly Gln Ala His Pro Gly Val Pro Glu Pro Phe Ala Lys Arg Glu Pro
                260                 265                270
Gly Glu Pro Val Leu Gly Ala Val His Val Gly His Ser Gly Glu Val
                275                 280                285
Gly Arg Gly Asp Gln Leu Pro Val Gln Pro Val Pro Gly Val Val
                290                 295                300
His Ala Leu Glu Gly Thr Leu Asp Arg Ala Arg Leu Leu Gly Ala Gln
305                 310                 315                320
Pro Gly Pro Ala Met Pro Ala His Ile Glu Glu Arg Pro Gln Pro Leu
                325                 330                335
Val Pro Ala Pro Gly Glu Gln His Ala Leu Pro Ser Tyr Leu Asp Gly
                340                 345                350
Leu Glu Val Ala Arg Arg Gly Gln Leu Gly Ala Ala His Gly Ala Glu
                355                 360                365
Pro Leu Gly Phe Glu Asp Pro Leu Leu Leu Pro Arg Glu Asp Pro Gly
                370                 375                380
Val Gly Val Val Pro Pro Gly Gln Arg Gly Gln Gln Ala Leu Arg Glu
385                 390                 395                400
Val Gly Gly Gly His Arg Arg Cys Ser Ser Arg Lys Gly Pro Asp Arg
                405                 410                415
Arg Met Arg Ala Gly Pro Lys Ala Asn Cys Ser Cys Cys Ala
                420                 425                430
```

<210> SEQ ID NO 11
<211> LENGTH: 69
<212> TYPE: PRT
<213> ORGANISM: Amycolatopsis sp.

<400> SEQUENCE: 11

Met Thr Ala Gln Pro Gly Phe Arg Ser His Arg Leu Tyr Gln Ser Ala
1               5                   10                  15

Arg Asp Glu Ala Val Phe Thr Glu Ile Ala Glu Trp Asp Ser Ala Glu
            20                  25                  30

Asp His Gln Arg Ala Thr Ala Gly Lys Gly Phe Arg Glu Pro Val Gly
        35                  40                  45

Glu Ala Met Lys His Ala Thr Ala Glu Pro Ala Pro Phe Val Leu Arg
    50                  55                  60

Ala Glu His Gly Ala
65

<210> SEQ ID NO 12
<211> LENGTH: 341
<212> TYPE: PRT
<213> ORGANISM: Amycolatopsis sp.

<400> SEQUENCE: 12

Met Thr Gly Thr Val Leu Pro Ala Ala Val Met Arg Val Arg Glu Leu
1               5                   10                  15

Ala Leu Ser Ala Ala Cys Ala Ala Ser Val Arg Ala Ala Lys Leu
            20                  25                  30

Gly Leu Ala Asp Val Leu Asp Asp Gln Pro Ala Thr Val Asp Glu Leu
        35                  40                  45

Ala Lys Ala Val His Ala Asp Pro Gly Ala Leu Arg Arg Leu Met Arg
    50                  55                  60

Ser Leu Thr Cys Phe Glu Val Phe Ala Glu Pro Glu Pro Asp Lys Phe
65                  70                  75                  80

Val His Thr Asp Ala Ser Arg Leu Leu Arg Glu Asp Ala Pro Arg Ser
                85                  90                  95

Leu Lys His Ile Leu Leu Trp Gly Thr Glu Pro Trp Thr Trp Glu Leu
            100                 105                 110

Trp Pro His Leu Asp Gln Ala Val Arg Thr Gly Lys Asn Val Phe Asp
        115                 120                 125

Asp Leu His Gly Lys Asp Phe Phe Glu Tyr Leu His Glu Gln Trp Pro
    130                 135                 140

Glu Ser Ala Glu Val Phe Asp Lys Ala Met Thr Gln Ser Ser Lys Leu
145                 150                 155                 160

Ser Ala Leu Ala Ile Ala Asp Arg Leu Asp Leu Thr Gly Ala Glu Arg
                165                 170                 175

Leu Ala Asp Ile Ala Gly Gly Gln Gly Asn Val Leu Ala Thr Leu Leu
            180                 185                 190

Ser Arg Asn Glu Lys Leu Asn Gly Val Leu Phe Asp Leu Pro Ala Val
        195                 200                 205

Val Ala Gly Ala Asp Glu Arg Leu Arg Val Gly Gly Ala Leu Ala Asp
    210                 215                 220

Arg Ala Glu Leu Val Ala Gly Asp Cys Arg Arg Glu Ile Pro Val Gln
225                 230                 235                 240

Ala Asp Val Tyr Leu Phe Lys Asn Ile Leu Glu Trp Asp Asp Glu Ser
                245                 250                 255

Thr Val Leu Ala Leu Arg Asn Ala Val Ala Ala Gly Arg Pro Gly Ala

```
              260                 265                 270
Arg Val Val Ile Ile Glu Asn Leu Val Asp Gly Thr Pro Glu Met Lys
            275                 280                 285

Phe Ala Thr Ala Met Asp Leu Leu Leu Leu Asn Val Gly Gly Lys
            290                 295                 300

Lys His Thr Lys Asp Gly Leu Leu Gly Leu Ile Gly Gln Ala Gly Leu
305                 310                 315                 320

Gln Val Asp Arg Val Ser Ala Val Asn Ser Tyr Leu His Met Val Glu
                325                 330                 335

Thr Thr Ile Pro Gly
            340

<210> SEQ ID NO 13
<211> LENGTH: 335
<212> TYPE: PRT
<213> ORGANISM: Amycolatopsis sp.

<400> SEQUENCE: 13

Val Thr Ala Lys Lys Leu His Glu Ile Met Arg Gly Tyr Val Lys Thr
1               5                   10                  15

Ala Leu Leu Arg Thr Ala Ile Glu Leu Asn Ile Phe Asp Gly Ile Gly
            20                  25                  30

Asp Arg Thr Val Asp Ala Asp Gly Leu Ala Arg Ala Leu Gly Val Asp
        35                  40                  45

Ala Arg Gly Leu Arg Ile Thr Leu Asp Ser Leu Ala Ala Ile Gly Leu
    50                  55                  60

Leu Arg Thr Val Asp Gly Lys Tyr Ala Leu Pro Val Asp Gly Asp Lys
65                  70                  75                  80

Phe Leu Leu Ser Ser Pro Thr Phe Phe Gly Pro Ser Leu Lys Leu
                85                  90                  95

Gly Ala Ser Asp Trp Glu Trp Asp Ala Gln Lys Arg Leu Thr Glu Ala
            100                 105                 110

Val Arg Lys Gly Gly Ala Val Met Asp Ser His Ala Leu Thr Pro Glu
        115                 120                 125

Phe Asp Tyr Trp Glu Asp Phe Ala Glu Asn Thr Thr Trp Phe Asn Asn
    130                 135                 140

Gly Ala Glu Leu Met Ala Glu Gln Leu Leu Pro Trp Ala Lys Asp
145                 150                 155                 160

Arg Asp Ser Val Asp Val Leu Asp Val Ala Cys Ser His Gly Tyr Tyr
                165                 170                 175

Gly Val Asn Leu Ala Lys Ala Glu Pro Lys Ala Arg Val Trp Gly Val
            180                 185                 190

Asp Trp Pro Asn Val Leu Pro Ile Thr Ala Lys Asn Tyr Glu Arg Asn
        195                 200                 205

Gly Ile Ser Asp Arg Phe Glu Gly Ile Pro Gly Asp Met Phe Ser Val
    210                 215                 220

Pro Leu Gly Gly Pro Tyr Asp Val Val Met Ile Thr Asn Val Leu His
225                 230                 235                 240

His Phe Ser Ala Asp Thr Ser Thr Asn Leu Leu Arg Arg Leu Phe Asp
                245                 250                 255

Val Leu Lys Pro Gly Gly Arg Ile Ala Val Thr Gly His Thr Phe Val
            260                 265                 270

Glu Gly Glu Arg Pro Glu Asp Lys Pro Leu Pro Tyr Leu Phe Ser Gln
        275                 280                 285

Ile Met Leu Val Met Thr Asp Glu Gly Glu Thr His Ser Thr Lys Thr
```

```
              290                 295                 300
Tyr Glu Arg Met Phe Thr Asp Ala Gly Phe Val Asn Pro Gln Ile Phe
305                 310                 315                 320

Thr Ala Glu Lys Ala Met His Thr Val Phe Thr Ala Asp Lys Ala
                325                 330                 335

<210> SEQ ID NO 14
<211> LENGTH: 433
<212> TYPE: PRT
<213> ORGANISM: Amycolatopsis sp.

<400> SEQUENCE: 14

Val Thr Leu Glu Leu Ala Gly Leu His Thr Gly Val Ser Asp Pro Arg
1               5                   10                  15

Met Asp Ser Met Arg Leu Leu Ser Glu Thr Ala Phe Arg Tyr Pro Gln
                20                  25                  30

Ala Val Ser Phe Ala Ser Gly Arg Pro Tyr Glu Gly Phe Phe Asp Ile
                35                  40                  45

Ala Lys Leu His His Tyr Leu Asp Arg Phe Val Glu His Leu Arg Glu
50                  55                  60

Arg Gly Met Pro Glu Glu Arg Ile Lys Lys Ala Leu Phe Gln Tyr Gly
65                  70                  75                  80

Pro Ile Asn Gly Leu Ile Arg Asp Met Ile Ala Arg Thr Leu Glu Val
                85                  90                  95

Asp Glu Asp Ile His Val Ala Pro Glu Ala Val Met Val Thr His Gly
                100                 105                 110

Cys Gln Glu Ala Met Met Ile Ala Leu Arg Gly Leu Phe Ala Ser Pro
            115                 120                 125

Ser Asp Val Leu Leu Thr Val Ser Pro Cys Tyr Val Gly Ile Ala Gly
            130                 135                 140

Ala Ala Lys Met Leu Asp Ile Pro Met Ala Ala Val Pro Glu Gly Ala
145                 150                 155                 160

Glu Gly Ile Asp Pro Glu Gln Val Ala Ala Val Ala Arg Glu Val Arg
                165                 170                 175

Ala Ser Gly Leu Arg Pro Val Ala Cys Tyr Val Thr Pro Asp Phe Ser
                180                 185                 190

Asn Pro Ser Gly His Ser Leu Pro Ile Ala Thr Arg His Arg Leu Leu
            195                 200                 205

Glu Val Ala Ala Glu Gln Asp Leu Leu Leu Glu Asp Asn Pro Tyr
            210                 215                 220

Gly Leu Phe Gly Arg Asp Gly Ala Gln Val Pro Thr Leu Lys Ala Leu
225                 230                 235                 240

Asp Thr Gln Arg Arg Val Ile Tyr Leu Gly Ser Phe Ala Lys Thr Val
                245                 250                 255

Phe Pro Gly Ala Arg Val Gly Tyr Leu Val Ala Asp Gln Glu Val Thr
                260                 265                 270

Gly Gly Pro Gly Ala Ala Lys Pro Leu Ala Glu Glu Leu Gly Lys Val
            275                 280                 285

Lys Ser Met Phe Thr Val Gly Thr Ser Gly Ile Ser Gln Ala Leu Val
            290                 295                 300

Gly Gly Val Leu Leu Asp Ala Asp Phe Ser Leu Arg Thr Ala Asn Arg
305                 310                 315                 320

Glu Leu Ala Asp Leu Tyr Val Arg His Leu Glu Val Thr Leu Ser Ser
                325                 330                 335

Leu Ala Glu His Phe Pro Pro Glu Arg Phe Ala Glu His Gly Val Arg
```

```
              340             345                 350
Trp Asn Val Pro Gly Gly Gly Phe Phe Leu Ser Val Glu Val Pro Phe
            355                 360                 365

Val Ala Gly Leu Glu Ala Leu Asp Arg Ser Ala Arg Asp His Gly Val
        370                 375                 380

Gly Trp Ala Pro Met Ser Met Phe Tyr Val Gly Asp Gly Gly Glu His
385                 390                 395                 400

Ile Val Arg Leu Gly Phe Ser Pro Leu Thr Ala Glu Glu Ile Arg Glu
                405                 410                 415

Gly Val Arg Arg Leu Ala Glu Phe Val Lys Ala Thr Pro Arg Thr Asp
            420                 425                 430

Arg

<210> SEQ ID NO 15
<211> LENGTH: 399
<212> TYPE: PRT
<213> ORGANISM: Amycolatopsis sp.

<400> SEQUENCE: 15

Met Arg Leu Leu Leu Val Thr Trp Asn Ala Pro Ala His Leu Phe Ala
1               5                   10                  15

Met Val Pro Leu Gly Trp Ala Ala Gln Val Ala Gly His Glu Val Arg
            20                  25                  30

Val Ala Ala Pro Pro Ser Cys Thr Glu Ala Ile Gly Arg Thr Gly Leu
        35                  40                  45

Thr Ala Val Pro Val Gly Thr Gln Arg Pro Ala Ala Pro Ser Gly Pro
    50                  55                  60

Pro Pro Gly Ala Pro Ser Gly Arg Trp Pro Val Asp Trp Ala Val His
65                  70                  75                  80

Pro Glu Leu Leu Asp Asp Ser Arg His Glu Leu Leu Arg Ser Leu Ala
                85                  90                  95

Ala Arg Gln Phe Ala Ala Ala Glu Pro Met Leu Asp Asp Leu Ile Glu
            100                 105                 110

Phe Ala Arg Trp Trp Ser Pro Asp Val Val Tyr Asp Pro Thr Ser
        115                 120                 125

Leu Ala Gly Glu Val Ala Ala Thr Val Leu Gly Val Pro Ala Phe Ala
    130                 135                 140

Cys Ser Trp Gly Arg Ala Ala Ala Val Arg Ile Glu Arg Gly Leu Gly
145                 150                 155                 160

Ser Glu Pro Leu Leu Gly Tyr Ala Arg Leu Phe Glu Arg Phe Gly Cys
                165                 170                 175

Gln Ala Pro Gln Gly Pro Ala Ser Trp Phe Asp Pro Phe Pro Ala Gly
            180                 185                 190

Leu Trp Leu Ala Glu Pro Asp Leu Pro Arg Gln Ala Met Arg Phe Val
        195                 200                 205

Pro Gly Thr Gly Gly Asp Ala Gly Ser Leu Pro Gly Trp Leu Arg Glu
    210                 215                 220

His Ser Ala Arg Pro Arg Ile Cys Val Thr Ser Ala Glu Pro Gly Gly
225                 230                 235                 240

Leu Leu Arg Pro Glu Ala Val Arg Ala Phe Tyr Arg His Ala Leu Thr
                245                 250                 255

Val Leu Ser Asp Val Asp Ala Glu Val Val Pro Ala Gly Pro Ala
            260                 265                 270

Ala Arg Thr Leu Leu Ala Glu Ile Pro His Thr Ala Arg Ile Val Asp
        275                 280                 285
```

Pro Val Ala Ala His Leu Leu Val Pro Ala Cys Arg Leu Thr Val His
            290                 295                 300

Gln Gly Asp Gly Leu Ser Thr Leu Ala Gly Leu Asn Ser Gly Val Pro
305                 310                 315                 320

Gln Tyr Val Leu Ala Pro Arg Pro Glu Gln Glu Leu Val Gly His Gln
                325                 330                 335

Leu His Arg Ala Gly Ala Gly Gly Tyr Arg Ser Leu Ser Glu Pro Val
            340                 345                 350

Asp Val Pro Ala Glu Arg Ala Val Leu Asp Ala Leu Leu Ala Pro Glu
            355                 360                 365

Ser Gly Gly Ala Ala Ala Arg Lys Leu Gln Glu Glu Thr Leu Ala Leu
370                 375                 380

Pro Leu Pro Ser Ala Val Leu Gly Arg Ile Glu Ser Ala Thr Arg
385                 390                 395

<210> SEQ ID NO 16
<211> LENGTH: 505
<212> TYPE: PRT
<213> ORGANISM: Amycolatopsis sp.

<400> SEQUENCE: 16

Met Pro Ser Gly Trp Ser Ser Pro Val Gly Arg Leu Leu Ser Gln Ala
1               5                   10                  15

Gly Leu Gly Leu Leu Ser Trp Val Val Pro Pro Ala Leu Val Asp Glu
            20                  25                  30

Ala Leu Ala Val Ala Gly Arg Asp Glu Arg Arg Phe Arg Ala Leu Pro
        35                  40                  45

Ser Arg Leu Gly Val Tyr Phe Val Leu Ala Leu Cys Leu Leu Arg Thr
50                  55                  60

Lys Ser Gly Asn Ala Thr Ile Arg Ala Met Phe Ser Gln Glu Ser Leu
65                  70                  75                  80

Pro Arg Leu Ser Val Leu Gly Trp Trp Pro Pro Ala Ser Thr Ala Leu
                85                  90                  95

Thr Lys Leu Arg Asp Arg Ile Gly Val Val Pro Phe Gln Leu Leu Phe
            100                 105                 110

Gly Ala Leu Ala Arg Ala Ala Pro Thr Arg Asn Arg Pro Trp Ser His
        115                 120                 125

Ala Phe Gly Leu Glu Val Cys Ala Trp Asp Gly Thr Glu Val Glu Pro
130                 135                 140

Ala Asp Thr Ala Ala Asn Arg Glu His Phe Pro His His Arg Thr
145                 150                 155                 160

Gly Val Ala Arg Gly Pro Ser Lys Ile Arg Val Leu Val Leu Leu Ser
                165                 170                 175

Cys Gly Ser Arg Arg Leu Leu Gly Ala Val Thr Gly Pro Leu Ser Gln
            180                 185                 190

Gly Glu Pro Thr Leu Ala Tyr Gln Leu Leu Pro Arg Leu His Asp Arg
        195                 200                 205

Met Leu Leu Leu Ala Asp Arg Cys Phe Leu Gly Tyr Pro Leu Trp Thr
210                 215                 220

Ala Ala Arg Glu Arg Gly Ala His Leu Leu Trp Arg Ala Lys Gln Asn
225                 230                 235                 240

Thr Pro Lys Leu Pro Val Gln His Ala Leu Pro Asp Glu Ser Trp Leu
                245                 250                 255

Ser Thr Leu His Ala Pro Ala Asp Ala Arg Arg Trp Ala Arg Asn Val
            260                 265                 270

Arg Arg Asn Lys Gln Arg Gly His Arg Pro Pro Thr Pro Arg Pro Ile
        275                 280                 285

Asn Gly Ile Val Val Arg Val Glu Ala Leu Ile Thr Val Thr Val
    290                 295                 300

Asp Gly Val Thr Arg Thr Glu Lys Tyr Arg Leu Val Thr Ser Leu Leu
305                 310                 315                 320

Asp Pro Ala His Ala Pro Ala Gly Gln Leu Val Ala Leu Tyr Ala Arg
            325                 330                 335

Arg Trp Thr Ala Glu Thr Gly Ile Lys Glu Ile Lys Thr Thr Leu Leu
            340                 345                 350

Ala Lys Arg Pro Leu Arg Gly His Thr Pro Ile Arg Ala Gln Gln Glu
        355                 360                 365

Leu Trp Ala Thr Leu Ile Val Tyr Gln Ala Ile Arg Leu Leu Ile Ser
370                 375                 380

His Ala Ala Leu Thr Gln Asn Leu Asp Pro Ser Arg Ile Ser Phe Thr
385                 390                 395                 400

Ser Ala Arg Asp Ala Ala Glu His Ala Ile Thr Thr Pro Ala Asp
            405                 410                 415

Thr Ser Arg His Leu Gln Trp Val Ala Gln Asp Leu Cys Arg Gln Leu
            420                 425                 430

Ile Thr Val His Thr His His Arg Val Tyr Pro Arg Ala Leu Lys Arg
            435                 440                 445

Thr Thr Thr Arg Tyr Pro His Arg Ser Lys Thr Pro Gln Pro Thr Ser
        450                 455                 460

Thr Lys Ala Ser Tyr Gln Val His Ile Leu Pro Thr Ala Glu Thr Thr
465                 470                 475                 480

Pro Pro Thr Thr Thr Lys Pro Thr Pro His Gln Pro Arg Thr Asp Leu
            485                 490                 495

Ser Ser Trp His Trp Thr Gln Ser Pro
            500                 505

<210> SEQ ID NO 17
<211> LENGTH: 481
<212> TYPE: PRT
<213> ORGANISM: Amycolatopsis sp.

<400> SEQUENCE: 17

Met Lys Asp Asn Leu Ala Arg Pro Asp Thr Val Gly Ala Asp Glu Asn
1               5                   10                  15

Arg Ile Ser Pro Ala Leu Trp Gly Leu Ala Ser Ile Leu Ile Leu Gly
            20                  25                  30

Gly Phe Thr Ser Met Phe Thr Ser Thr Ile Val Asn Val Ala Leu Asp
        35                  40                  45

Thr Leu Ser Gln Lys Leu Ser Ala Pro Leu Gly Thr Val Gln Trp Thr
    50                  55                  60

Ala Thr Gly Tyr Leu Met Ala Leu Ala Thr Ala Val Pro Val Ser Gly
65              70                  75                  80

Trp Ala Ser Lys Arg Tyr Gly Ala Thr Arg Leu Trp Leu Gly Ser Val
                85                  90                  95

Ala Leu Phe Thr Leu Phe Ser Ala Leu Cys Ala Leu Ser Thr Ser Val
            100                 105                 110

Glu Met Leu Ile Thr Phe Arg Val Leu Gln Gly Ile Ala Gly Gly Leu
        115                 120                 125

Leu Val Pro Ala Gly Gln Ile Leu Leu Val Thr Ala Ala Gly Pro Lys
    130                 135                 140

```
Arg Ile Gly Arg Met Leu Thr Ala Val Ser Val Pro Ile Tyr Leu Ala
145                 150                 155                 160

Pro Ala Val Gly Thr Thr Leu Gly Ser Val Leu Thr Gln Gly Leu Gly
            165                 170                 175

Trp Pro Trp Leu Phe Trp Ile Thr Val Pro Leu Gly Ala Leu Gly Phe
            180                 185                 190

Phe Ala Gly Leu Arg Trp Leu Pro Lys Ala Pro Pro Lys Gly Ala Pro
            195                 200                 205

Ala Leu Asp Val Arg Gly Leu Ile Ile Leu Val Ala Gly Leu Pro Leu
            210                 215                 220

Leu Thr Tyr Gly Val Ala Gly Ile Gly Glu Asn Gly Gly Arg Thr Glu
225                 230                 235                 240

Thr Ile Ala Val Ile Ala Ala Val Ala Gly Ala Leu Leu Leu Ala Leu
            245                 250                 255

Phe Thr Leu His Ala Val Arg Ser Arg Asn Pro Leu Leu Asn Leu Arg
            260                 265                 270

Leu Phe Lys Asp Arg Ala Phe Ser Ser Ala Ala Val Val Ile Phe Cys
            275                 280                 285

Met Gly Ile Ala Leu Phe Gly Ala Met Ile Val Leu Pro Ile Tyr Phe
            290                 295                 300

Leu Gln Val Arg His Glu Asp Leu Val Thr Ala Gly Leu Leu Thr Ala
305                 310                 315                 320

Pro Ser Ala Ile Gly Thr Val Leu Ala Leu Pro Leu Ala Gly Lys Met
            325                 330                 335

Thr Asp Lys Ile Gly Gly Ala Arg Val Ile Phe Ala Gly Leu Val Val
            340                 345                 350

Thr Ile Ile Gly Thr Ile Pro Leu Ala Leu Val Thr Pro His Asp Ser
            355                 360                 365

Tyr Val Trp Leu Ser Leu Val Gln Ile Val Arg Gly Ile Gly Ile Gly
            370                 375                 380

Met Thr Thr Thr Pro Ala Met Ala Ala Gly Leu Ala Met Ile Gly Lys
385                 390                 395                 400

Glu Asp Val Pro His Ala Thr Pro Ile Phe Asn Val Leu Gln Arg Val
            405                 410                 415

Gly Gly Ser Phe Gly Thr Ala Leu Thr Thr Val Leu Val Ala Phe Gln
            420                 425                 430

Leu Ala Ser Gly Pro Gln Thr Asp Glu Gly Ala Ala Asp Ala Ile Gly
            435                 440                 445

Tyr Thr His Trp Trp Ile Val Ala Cys Thr Ala Ile Val Leu Ile Pro
            450                 455                 460

Ser Met Leu Leu Val Gln Val Glu Ser Arg Arg Arg Gln Ala Ala Ala
465                 470                 475                 480

Ala

<210> SEQ ID NO 18
<211> LENGTH: 190
<212> TYPE: PRT
<213> ORGANISM: Amycolatopsis sp.

<400> SEQUENCE: 18

Val Arg Leu Ser Pro Glu Thr Phe Ala Arg Ala Ala Leu Lys Leu Leu
1               5                   10                  15

Asn Lys Ser Gly Leu Glu Gly Val Ser Leu Arg Lys Leu Gly Asp Glu
            20                  25                  30
```

```
Leu Gly Val Gln Gly Pro Ala Leu Tyr Ala His Phe Lys Asn Lys Gln
         35                  40                  45

Glu Leu Leu Asp Leu Met Ala Glu Ile Met Leu Asp Glu Ala Leu Ala
 50                  55                  60

Pro Leu Asp Ala Met Thr Glu Val Ala Asp Trp His Trp Trp Leu Ala
 65                  70                  75                  80

Glu Arg Ala Arg Thr Ile Arg Arg Thr Leu Leu Ser Tyr Arg Asp Gly
                 85                  90                  95

Ala Leu Leu His Ala Gly Ser Arg Pro Thr Ala Asp Gly Ala Glu Ala
            100                 105                 110

Ile Pro Ala Leu Leu Arg Pro Leu Arg Glu Ala Gly Phe Ser Asp Lys
        115                 120                 125

Glu Ala Leu Thr Val Ile Ile Thr Ile Gly Arg Tyr Thr Leu Gly Cys
130                 135                 140

Val Ile Asp Glu Gln Arg Pro Gly Glu Pro Ala Pro Gln Pro Gly Pro
145                 150                 155                 160

Gly Ala Asp Asp Thr Phe Glu Phe Gly Leu Gln Ala Leu Leu Ala Gly
                165                 170                 175

Leu Arg Ala Arg Leu Pro Glu Arg Val Pro Asp Ser Ala Gly
            180                 185                 190

<210> SEQ ID NO 19
<211> LENGTH: 612
<212> TYPE: PRT
<213> ORGANISM: Streptomyces rimosus

<400> SEQUENCE: 19

Met Cys Gly Ile Ala Gly Trp Ile Asp Phe Glu Arg Asn Leu Ala Gln
1               5                   10                  15

Glu Arg Ala Thr Ala Trp Ala Met Thr Asp Thr Met Ala Cys Arg Gly
            20                  25                  30

Pro Asp Asp Ala Gly Leu Trp Thr Gly His Ala Ala Leu Gly His
         35                  40                  45

Arg Arg Leu Ala Val Ile Asp Pro Ala His Gly Arg Gln Pro Met His
 50                  55                  60

Ser Thr Leu Pro Asp Gly Thr Ser His Val Ile Thr Phe Ser Gly Glu
 65                  70                  75                  80

Ile Tyr Asn Phe Arg Glu Leu Arg Val Glu Leu Glu Ser Gln Gly His
                 85                  90                  95

Arg Phe Arg Thr His Cys Asp Thr Glu Val Val Leu His Gly Tyr Thr
            100                 105                 110

Arg Trp Gly Arg Glu Leu Val Asp Arg Leu Asn Gly Met Tyr Ala Phe
        115                 120                 125

Ala Val Trp Asp Glu Ala Arg Gln Glu Leu Leu Leu Val Arg Asp Arg
130                 135                 140

Met Gly Val Lys Pro Leu Tyr Tyr His Pro Thr Ala Thr Gly Val Leu
145                 150                 155                 160

Phe Gly Ser Glu Pro Lys Ala Val Leu Ala His Pro Ser Leu Arg Arg
                165                 170                 175

Arg Val Thr Ala Glu Gly Leu Cys Glu Val Leu Asp Met Val Lys Thr
            180                 185                 190

Pro Gly Arg Thr Val Phe Ser Gly Met Arg Glu Val Leu Pro Gly Glu
        195                 200                 205

Met Val Thr Val Gly Arg Ser Gly Val Ala Arg Arg Tyr Trp Thr
210                 215                 220
```

-continued

Leu Gln Ala Arg Glu His Thr Asp Asp Leu Glu Thr Thr Ile Ala Thr
225                 230                 235                 240

Val Arg Gly Leu Leu Thr Asp Arg Val Arg Arg Gln Leu Val Ser Asp
            245                 250                 255

Val Pro Leu Cys Thr Leu Leu Ser Gly Gly Leu Asp Ser Ser Ala Val
        260                 265                 270

Thr Ala Leu Ala Ala Arg Ala Gly Asp Gly Pro Val Arg Thr Phe Ser
    275                 280                 285

Val Asp Phe Ser Gly Ala Gly Thr Arg Phe Gln Pro Asp Ala Val Arg
290                 295                 300

Gly Asn Thr Asp Ala Pro Tyr Val Gln Glu Met Val Arg His Val Ala
305                 310                 315                 320

Ala Asp His Thr Glu Val Val Leu Asp Ser Ala Asp Leu Ala Ala Pro
            325                 330                 335

Glu Val Arg Ala Ala Val Leu Gly Ala Thr Asp Leu Pro Pro Ala Phe
        340                 345                 350

Trp Gly Asp Met Trp Pro Ser Leu Tyr Leu Phe Arg Gln Val Arg
    355                 360                 365

Gln His Cys Thr Val Ala Leu Ser Gly Glu Ala Ala Asp Glu Leu Phe
370                 375                 380

Gly Gly Tyr Arg Trp Phe His Arg Thr Ala Ala Ile Asp Ala Gly Thr
385                 390                 395                 400

Phe Pro Trp Leu Thr Ala Gly Ser Ala Arg Tyr Gly Gly Arg Gly
            405                 410                 415

Leu Phe Asp Arg Lys Leu Leu Asp Lys Leu Asp Leu Pro Gly Tyr Gln
        420                 425                 430

Arg Asp Arg Tyr Ala Glu Ala Arg Lys Glu Val Pro Val Leu Pro Gly
    435                 440                 445

Glu Asp Ala Arg Glu Ala Glu Leu Arg Arg Val Thr Tyr Leu Asn Leu
450                 455                 460

Thr Arg Phe Val Gln Thr Leu Leu Asp Arg Lys Asp Arg Met Ser Met
465                 470                 475                 480

Ala Thr Gly Leu Glu Val Arg Val Pro Phe Cys Asp His Arg Leu Val
            485                 490                 495

Asp Tyr Val Phe Asn Val Pro Trp Ala Met Lys Ser Phe Asp Gly Arg
        500                 505                 510

Glu Lys Ser Leu Leu Arg Ala Ala Val Arg Asp Leu Leu Pro Glu Ser
    515                 520                 525

Val Val Thr Arg Val Lys Thr Pro Tyr Pro Ala Thr Gln Asp Pro Val
530                 535                 540

Tyr Glu Arg Leu Leu Arg Asp Glu Leu Ala Ala Leu Leu Ala Asp Ser
545                 550                 555                 560

Gln Ala Pro Val Arg Glu Leu Leu Asp Leu Gly Arg Ala Arg Asp Leu
            565                 570                 575

Leu Arg Arg Pro Val Gly Ala Val Ser Gln Pro Tyr Asp Arg Gly Ser
        580                 585                 590

Leu Glu Leu Val Leu Trp Met Asn Thr Trp Leu Ala Glu Tyr Gly Val
    595                 600                 605

Ser Leu Glu Leu
    610

<210> SEQ ID NO 20
<211> LENGTH: 344
<212> TYPE: PRT
<213> ORGANISM: Streptomyces rimosus

<400> SEQUENCE: 20

```
Met Thr Thr Thr Pro Leu Ala Pro Val Ala Gln Ala Arg Ser Leu Leu
1               5                   10                  15

Gln Leu Thr Thr Ala Tyr His Gln Ala Lys Ala Leu His Ser Ala Val
            20                  25                  30

Glu Leu Gly Leu Phe Asp Leu Ala Asp Gly Pro Ala Thr Ala Glu
        35                  40                  45

Glu Val Lys Asp Arg Leu Arg Ile Val His Pro Leu Ala Lys Glu Phe
    50                  55                  60

Leu Asp Ala Leu Val Ala Leu Glu Leu Leu Glu Ala Asp Gly Asp Arg
65                  70                  75                  80

Tyr Arg Asn Ser Pro Ala Ala Gln Ala Phe Leu Val Ser Gly Ala Ser
                85                  90                  95

Glu Tyr Leu Gly Gly Thr Val Leu Gln His Ala Arg Lys His Tyr His
            100                 105                 110

Val Trp Ala Gly Leu Thr Thr Ala Leu Gln Glu Gly Glu Ala Gly Ser
        115                 120                 125

Gly Ala Glu Ala His Gly Pro Glu Ala Tyr Pro Lys His Tyr Glu Asp
130                 135                 140

Pro Glu Arg Ala Arg Gln Val Met Ala His Phe Asp Thr Phe Ser Ser
145                 150                 155                 160

Phe Thr Ala Glu Glu Leu Ala Arg Arg Val Asp Trp Ser Gly Tyr Gly
                165                 170                 175

Ser Phe Ile Asp Ile Gly Gly Ala Arg Gly Asn Leu Ala Thr Arg Val
            180                 185                 190

Ala Leu Ala His Pro His Leu His Gly Ala Val Phe Asp Leu Pro Ala
        195                 200                 205

Leu Ala Pro Leu Ala Gly Glu Leu Ile Arg Glu Arg Gly Leu Glu Gly
    210                 215                 220

Arg Val Arg Phe His Gly Gly Asp Phe Leu Thr Asp Pro Leu Pro Ser
225                 230                 235                 240

Ala Asp Ala Val Val Thr Gly His Val Leu Pro Asp Trp Pro Val Pro
                245                 250                 255

Gln Arg Arg Lys Leu Leu Ala Arg Ile His Glu Ala Leu Pro Ser Gly
            260                 265                 270

Gly Ala Leu Val Val Tyr Asp Leu Met Thr Asp Pro Ala Thr Thr Thr
        275                 280                 285

Val His Asp Val Leu Gln Arg Leu Asn His Gly Leu Ile Arg Gly Asp
    290                 295                 300

Ser Ser Ser Ser Ser Val Glu Glu Tyr Arg Ala Glu Ile Glu Glu Ala
305                 310                 315                 320

Gly Phe Arg Val Arg Gln Ala Glu Arg Ile Asp Asn Leu Leu Gly Asp
                325                 330                 335

Trp Leu Ile Val Ala Val Lys Pro
            340

<210> SEQ ID NO 21
<211> LENGTH: 418
<212> TYPE: PRT
<213> ORGANISM: Streptomyces rimosus

<400> SEQUENCE: 21

Met Thr Gly His Pro Arg Pro Pro Ala Asp Gly Ala His Thr Asp Val
1               5                   10                  15
```

Cys Val Val Gly Gly Pro Ala Gly Leu Thr Leu Ala Leu Leu Met
            20              25              30

Leu Arg Ser Gly Ala Arg Val Thr Leu Val Glu Arg Ser Arg Ser Leu
        35              40              45

Asp Arg Ala Tyr Arg Gly Glu Ile Leu Gln Pro Gly Gly Gln Ala Leu
 50              55              60

Leu Asp Ala Leu Gly Val Leu Glu Gly Ala Arg Arg Gly Cys His
65              70              75              80

Glu His Asp Gly Phe Arg Leu Glu Glu Arg Gly Arg Thr Leu Ile Asn
            85              90              95

Gly Asp Tyr Arg Arg Leu Pro Gly Pro Tyr Asn Cys Leu Leu Ser Leu
        100             105             110

Pro Gln Gln His Leu Leu Thr Asp Leu Leu Glu Arg Cys Arg Ala His
        115             120             125

Pro Arg Phe Thr Cys Leu Thr Gly Thr Lys Val Asn Gly Leu Val Glu
        130             135             140

Glu Gly Gly Val Val Arg Gly Val Val Cys Gly Gly Ala Asp Gly
145             150             155             160

Leu Val Val Arg Ala Asp Cys Val Val Gly Ala Asp Gly Arg Tyr Ser
                165             170             175

Thr Val Arg Lys Leu Ala Gly Ile Pro Tyr Asp Arg Ile Glu Leu Phe
            180             185             190

Asp Gln Asp Val Leu Trp Cys Lys Leu Thr Ala Pro Ala Thr Arg Thr
        195             200             205

Val Arg Ile Phe Arg Ala Gly Gly Asn Pro Val Leu Ala Tyr Thr Ser
        210             215             220

Phe Pro Asp Cys Val Gln Leu Gly Trp Thr Leu Pro His Lys Gly Tyr
225             230             235             240

Gln Ala Leu Ala Glu Arg Gly Phe Ala His Val Lys Glu Arg Ile Arg
                245             250             255

Ala Ala Val Pro Glu Tyr Ala Asp Thr Val Asp Gln Gln Leu Asn Ser
            260             265             270

Phe Lys Asp Val Ser Leu Leu Asp Val Phe Ala Gly Ser Ala Arg Arg
        275             280             285

Trp Ala Arg Asp Gly Leu Leu Leu Ile Gly Asp Ser Ala His Thr His
290             295             300

Ser Pro Ile Gly Ala Gln Gly Ile Asn Leu Ala Ile Gln Asp Ala Val
305             310             315             320

Ala Ala His Pro Val Leu Cys Glu Gly Leu Arg Arg Asp Leu Ser
                325             330             335

Glu Arg Phe Leu Asp Ala Val Ala Ala Arg Arg Pro Glu Thr Glu
            340             345             350

Arg Ala Thr Arg Val Gln Val Met Gln Ser Arg Met Met Leu Ser Thr
        355             360             365

Gly Arg Val Ser Ala Ala Val Arg Pro Lys Ala Ala Met Leu Val Ser
        370             375             380

Arg Thr Pro Ala Tyr Arg Ser Val Leu Arg Arg Ile Ala Tyr Gly Asp
385             390             395             400

Gln Thr Leu Arg Val Arg Ser Asp Leu Phe Glu Glu Gly Glu Pro Ala
                405             410             415

Thr Val

<210> SEQ ID NO 22
<211> LENGTH: 557

```
<212> TYPE: PRT
<213> ORGANISM: Streptomyces rimosus

<400> SEQUENCE: 22

Met Pro Pro Glu Ala Asp Gly Pro Gln Val Leu Ile Ala Gly Ala Gly
1               5                   10                  15

Pro Val Gly Leu Thr Leu Ala His Glu Leu Thr Arg Arg Val Arg
            20                  25                  30

Val Arg Val Ile Asp Arg Ala Asp Gly Pro Ala Thr Thr Ser Arg Ala
            35                  40                  45

Leu Ala Val His Pro Arg Thr Leu Glu Ala Cys His Gln Met Gly Leu
50                  55                  60

Ala Asp Ala Leu Val Ala Arg Gly Arg Pro Val Val His Phe Thr Val
65                  70                  75                  80

His Leu Arg Gly Arg Gln Leu Ile Arg Phe Asp Thr Asn Tyr Gly Arg
                85                  90                  95

Leu Pro Thr Ala Tyr Pro Phe Ser Leu Met Leu Asp Gln Val Arg Thr
            100                 105                 110

Glu Glu Ile Leu Arg Glu Arg Leu Ala Gly Leu Gly Val Gly Ile Glu
            115                 120                 125

Trp Gly Val Glu Leu Ala Asp Cys Ala Pro Cys Gly Asp Arg Val Asn
130                 135                 140

Ala Glu Leu Arg Arg Asp Gly Arg Ser Glu Gln Val Thr Val Pro Trp
145                 150                 155                 160

Leu Val Gly Ala Asp Gly Ser Arg Ser Thr Val Arg Glu Arg Leu Gly
                165                 170                 175

Leu Arg Leu Val Gly Asp Ala Thr Gln Thr Trp Leu Asn Ala Asp Val
            180                 185                 190

Val Leu Asp Ala Asp Leu Ser Arg Asp Ser Asn His Leu Val His Thr
            195                 200                 205

Gly Ser Gly Thr Val Leu Leu Val Pro Phe Pro Asp Pro Gly Lys Trp
210                 215                 220

Arg Ala Val Asp Thr Gly Tyr Ala Gly Gln Gly Ala Asp Pro Glu Thr
225                 230                 235                 240

Val Arg Arg Arg Leu Ala Gly Ser Leu Ala Arg Gly Leu Gly Arg Pro
                245                 250                 255

Val Ala Val Ser Glu Pro Thr Trp Val Ser Val Phe Arg Val Gln Gln
            260                 265                 270

Arg Met Ile Thr Ala Met Arg Ser Gly Arg Cys Phe Val Ala Gly Asp
            275                 280                 285

Ala Ala His Val His Ser Pro Ala Ser Gly Gln Gly Met Asn Thr Gly
290                 295                 300

Met Gln Asp Ala Tyr Asn Leu Ala Trp Lys Leu Ala Asp Val Val Arg
305                 310                 315                 320

Gly His Ala Arg Glu Leu Leu Asp Thr Tyr Ala Ala Glu Arg Ile
                325                 330                 335

Pro Val Gly Gly Arg Leu Leu Ser Ser Thr Arg Thr Ala Thr Ala Leu
            340                 345                 350

Val Ala Leu Arg Asn Ala Val Ala Pro Val Ala Met Pro Val Gly Leu
            355                 360                 365

Ser Phe Leu Lys Ala Val Arg Pro Leu Lys Arg Val Glu His Arg
370                 375                 380

Ile Met Ala Gly Met Ser Gly Leu Ala Leu His Tyr Ala Asp Ser Pro
385                 390                 395                 400
```

```
Leu Thr Tyr Gly Thr Gly Asp Gly Ala Ala Gly Val His Pro Gly His
                405                 410                 415

Leu Val Ala Cys Thr Glu Gln Asp Val Ala Arg His Pro Gly Leu Arg
            420                 425                 430

Ala Leu Arg Gln Ala Leu Thr Asp Pro Arg Trp Leu Leu Leu Leu Phe
        435                 440                 445

Ala Asp Asp Gly Gly Ala Ala Glu Leu Ala Leu Arg Tyr Gly Arg Ala
    450                 455                 460

Val Gln Ile Arg Thr Val Ile Pro His Glu Asp Glu Asp Gly Pro Ala
465                 470                 475                 480

Leu Ala Asp Pro Asp Asp Ala Leu Arg Gln Thr Leu Gly Val Pro Pro
                485                 490                 495

Gly Gly Trp Ala Leu Ile Arg Pro Asp Gly Tyr Leu Ala Ala Lys Gly
            500                 505                 510

Gln Arg Ser Gly Thr Thr Thr Leu Thr Ala Arg Leu Gln Ala Leu His
        515                 520                 525

Leu Leu Pro Glu Asp Thr Ala Pro Gly Ala Gly Asp Ser Ala Gly Arg
    530                 535                 540

Pro Ala Pro Asp Gly Thr Arg Arg Gly Val Thr Thr Glu
545                 550                 555

<210> SEQ ID NO 23
<211> LENGTH: 503
<212> TYPE: PRT
<213> ORGANISM: Streptomyces rimosus

<400> SEQUENCE: 23

Met Arg Tyr Asp Val Val Ile Ala Gly Ala Gly Pro Thr Gly Leu Met
1               5                   10                  15

Leu Ala Cys Glu Leu Arg Leu Ala Gly Ala Arg Thr Leu Val Leu Glu
            20                  25                  30

Arg Leu Ala Glu Pro Val Asp Phe Ser Lys Ala Leu Gly Val His Ala
        35                  40                  45

Arg Thr Val Glu Leu Leu Asp Met Arg Gly Leu Gly Glu Gly Phe Gln
    50                  55                  60

Ala Glu Ala Pro Lys Leu Arg Gly Gly Asn Phe Ala Ser Leu Gly Val
65                  70                  75                  80

Pro Leu Asp Phe Ser Ser Phe Asp Thr Arg His Pro Tyr Ala Leu Phe
                85                  90                  95

Val Pro Gln Val Arg Thr Glu Glu Leu Leu Thr Gly Arg Ala Leu Glu
            100                 105                 110

Leu Gly Ala Glu Leu Arg Arg Gly His Ala Val Thr Ala Leu Glu Gln
        115                 120                 125

Asp Ala Asp Gly Val Thr Val Ser Val Thr Gly Pro Glu Gly Pro Tyr
    130                 135                 140

Glu Val Glu Cys Ala Tyr Leu Val Gly Cys Asp Gly Gly Gly Ser Thr
145                 150                 155                 160

Val Arg Lys Leu Leu Gly Ile Asp Phe Pro Gly Gln Asp Pro His Met
                165                 170                 175

Phe Ala Val Ile Ala Asp Ala Arg Phe Arg Glu Glu Leu Pro His Gly
            180                 185                 190

Glu Gly Met Gly Pro Met Arg Pro Tyr Gly Val Met Arg His Asp Leu
        195                 200                 205

Arg Ala Trp Phe Ala Ala Phe Pro Leu Glu Pro Asp Val Tyr Arg Ala
    210                 215                 220
```

-continued

Thr Val Ala Phe Phe Asp Arg Pro Tyr Ala Asp Arg Arg Ala Pro Val
225                 230                 235                 240

Thr Glu Glu Asp Val Arg Ala Ala Leu Thr Glu Val Ala Gly Ser Asp
            245                 250                 255

Phe Gly Met His Asp Val Arg Trp Leu Ser Arg Leu Thr Asp Thr Ser
        260                 265                 270

Arg Gln Ala Glu Arg Tyr Arg Asp Gly Arg Val Leu Leu Ala Gly Asp
    275                 280                 285

Ala Cys His Ile His Leu Pro Ala Gly Gln Gly Leu Asn Leu Gly
290                 295                 300

Phe Gln Asp Ala Val Asn Leu Gly Trp Lys Leu Gly Ala Thr Ile Ala
305                 310                 315                 320

Gly Thr Ala Pro Pro Glu Leu Leu Asp Thr Tyr Glu Ala Glu Arg Arg
                325                 330                 335

Pro Ile Ala Ala Gly Val Leu Arg Asn Thr Arg Ala Gln Ala Val Leu
            340                 345                 350

Ile Asp Pro Asp Pro Arg Tyr Glu Gly Leu Arg Glu Leu Met Ile Glu
        355                 360                 365

Leu Leu His Val Pro Glu Thr Asn Arg Tyr Leu Ala Gly Leu Ile Ser
    370                 375                 380

Ala Leu Asp Val Arg Tyr Pro Met Ala Gly Glu His Pro Leu Leu Gly
385                 390                 395                 400

Arg Arg Val Pro Asp Leu Pro Leu Val Thr Glu Asp Gly Thr Arg Gln
                405                 410                 415

Leu Ser Thr Tyr Phe His Ala Arg Gly Val Leu Leu Thr Leu Gly
            420                 425                 430

Cys Asp Gln Pro Leu Ala Asp Glu Ala Ala Trp Lys Asp Arg Val
        435                 440                 445

Asp Leu Val Ala Ala Glu Gly Val Ala Asp Pro Gly Ser Ala Val Asp
450                 455                 460

Gly Leu Thr Ala Leu Leu Val Arg Pro Asp Gly Tyr Ile Cys Trp Thr
465                 470                 475                 480

Ala Ala Pro Glu Thr Gly Thr Asp Gly Leu Thr Asp Ala Leu Arg Thr
                485                 490                 495

Trp Phe Gly Pro Pro Ala Met
            500

<210> SEQ ID NO 24
<211> LENGTH: 95
<212> TYPE: PRT
<213> ORGANISM: Streptomyces rimosus

<400> SEQUENCE: 24

Met Phe Thr Phe Ile Asn Arg Phe Thr Val Gln Gly Asp Ala Ala Glu
1               5                   10                  15

Phe Glu Lys Arg Val Gly Glu Ile Thr Ala His Met Ser Arg Gln Pro
            20                  25                  30

Gly Phe Arg Ser His Arg Leu Leu Arg Ser Ala Lys Asp Pro Gln Val
        35                  40                  45

Tyr Val Glu Ile Ala Glu Trp Asp Asp Ala Glu Ser His Gly Arg Ala
    50                  55                  60

Leu Arg Thr Glu Thr Phe Gln Gln Ala Val Ser Glu Val Lys Lys Leu
65                  70                  75                  80

Ala Ser Ala Asp Pro Ala Pro Phe Val Pro Val Thr Ala Gly
                85                  90                  95

```
<210> SEQ ID NO 25
<211> LENGTH: 452
<212> TYPE: PRT
<213> ORGANISM: Streptomyces aurefaciens

<400> SEQUENCE: 25

Met Phe His Arg Asp Gly Glu Glu Pro Asp Pro Asn Glu Thr Ser Gln
1               5                   10                  15

Phe Arg Ile Pro Ser Ile Val Gly Asn Ala Ala His Phe Phe Arg Gln
            20                  25                  30

Asp Thr Asp Ser Tyr Met Phe His Ala Ala Val Arg Tyr Gly Cys Asp
        35                  40                  45

Ala Arg Gln Tyr Tyr Arg Val Glu Asn Ile Glu Phe Asp Asp Gly Gly
    50                  55                  60

Val Thr Val Ser Gly Ala Asp Gly Ser Thr Val Arg Ala Arg Tyr Leu
65                  70                  75                  80

Val Asp Ala Ser Gly Phe Arg Ser Pro Leu Ala Arg Gln Leu Gly Leu
                85                  90                  95

Arg Glu Glu Pro Ser Arg Leu Lys His His Ala Arg Ser Ile Phe Thr
            100                 105                 110

His Met Val Gly Val Asp Ala Ile Asp Asp His Val Asp Met Pro Ala
        115                 120                 125

Glu Leu Arg Pro Pro Val Pro Trp Asn Asp Gly Thr Met His His Ile
    130                 135                 140

Phe Glu Arg Gly Trp Met Trp Ile Ile Pro Phe Asn Asn His Pro Gly
145                 150                 155                 160

Ala Thr Asn Pro Leu Cys Ser Val Gly Ile Gln Leu Asp Glu Arg Arg
                165                 170                 175

Tyr Pro Ala Arg Pro Asp Leu Thr Pro Glu Glu Phe Arg Ser His
            180                 185                 190

Val Asp Arg Phe Pro Ala Val Gln Arg Gln Leu Lys Gly Ala Arg Ser
        195                 200                 205

Val Arg Glu Trp Val Arg Thr Asp Arg Met Gln Tyr Ser Ser Ser Arg
    210                 215                 220

Thr Val Gly Glu Arg Trp Cys Leu Met Ser His Ala Ala Gly Phe Ile
225                 230                 235                 240

Asp Pro Leu Phe Leu Arg Gly Leu Ser Asn Thr Cys Glu Ile Ile Asn
                245                 250                 255

Ala Leu Ser Trp Arg Leu Met Ala Ala Leu Arg Glu Asp Asp Phe Ala
            260                 265                 270

Val Glu Arg Phe Ala Tyr Val Glu Glu Leu Glu Gln Gly Leu Leu Asp
        275                 280                 285

Trp Asn Asp Lys Leu Val Asn Asn Ser Phe Ile Ser Phe Ser His Tyr
    290                 295                 300

Pro Leu Trp Asn Ser Ala Phe Arg Ile Trp Ala Ser Ala Ser Val Ile
305                 310                 315                 320

Gly Gly Lys Arg Ile Leu Asn Ala Leu Thr Arg Thr Lys Glu Thr Gly
                325                 330                 335

Asp Asp Ser His Cys Gln Ala Leu Asp Asp Asn Pro Tyr Pro Gly Leu
            340                 345                 350

Trp Cys Pro Leu Asp Phe Tyr Lys Glu Ala Phe Asp Glu Leu Thr Glu
        355                 360                 365

Leu Cys Glu Ala Val Asp Ala Gly His Thr Thr Ala Glu Glu Ala Ala
    370                 375                 380
```

```
Arg Leu Leu Glu Gln Arg Val Arg Glu Ser Asp Trp Met Leu Pro Ala
385                 390                 395                 400

Leu Gly Phe Asn Asp Pro Asp Thr His His Ile Asn Pro Thr Ala Asp
            405                 410                 415

Lys Met Ile Arg Ile Ala Glu Trp Ala Thr Gly His His Arg Pro Glu
        420                 425                 430

Ile Arg Glu Leu Leu Ala Ala Ser Ala Glu Glu Val Arg Ala Ala Met
            435                 440                 445

Arg Val Lys Pro
        450

<210> SEQ ID NO 26
<211> LENGTH: 339
<212> TYPE: PRT
<213> ORGANISM: Streptomyces glaucescens

<400> SEQUENCE: 26

Met Thr Pro His Thr His Val Arg Gly Pro Gly Asp Ile Leu Gln Leu
1               5                   10                  15

Thr Met Ala Phe Tyr Gly Ser Arg Ala Leu Ile Ser Ala Val Glu Leu
            20                  25                  30

Asp Leu Phe Thr Leu Leu Ala Gly Lys Pro Leu Pro Leu Gly Glu Leu
        35                  40                  45

Cys Glu Arg Ala Gly Ile His Pro Arg Gly Ala Arg Asp Phe Leu Asp
    50                  55                  60

Ala Leu Val Ala Leu Gly Leu Leu Glu Arg Glu Gly Glu Asp Thr Tyr
65                  70                  75                  80

Arg Asn Ser Pro Ala Ala Asp Arg His Leu Asp Arg Arg Lys Pro Gly
                85                  90                  95

Tyr Val Gly Gly Tyr Ala Arg Leu Ala Asp Thr Lys Leu Phe Pro Val
            100                 105                 110

Trp Ala Arg Leu Thr Glu Ala Leu Arg Thr Gly Glu Lys Gln Val Pro
        115                 120                 125

Ser Gln Gly Gly Phe Phe Gly Gly Tyr Ala Asp Pro Glu Ala Ala Arg
    130                 135                 140

Gly Phe Leu Gly Ala Met Asp Ala Val Asn Gly Gly Val Gly His Ser
145                 150                 155                 160

Leu Ala Gly Ala Leu Asp Trp Thr Glu Tyr Ser Ser Phe Val Asp Leu
                165                 170                 175

Gly Gly Ala Arg Gly Asn Leu Ala Ala His Leu His Arg Ala His Pro
            180                 185                 190

His Leu Arg Ala Thr Cys Phe Asp Leu Pro Glu Met Glu Pro Phe Phe
        195                 200                 205

Gln Glu His Met Lys Ser Leu Glu Thr Thr Asp Gln Val Arg Phe Ala
    210                 215                 220

Gly Gly Asp Phe Phe Thr Asp Pro Leu Pro Arg Ala Asp Val Phe Ile
225                 230                 235                 240

Val Gly His Ile Leu His Tyr Phe Gly Leu Arg Gln Arg Glu Ala Leu
                245                 250                 255

Ile Ala Arg Ile His Gln Ala Leu Thr Pro Gly Gly Ala Val Leu Val
            260                 265                 270

Tyr Asp Arg Met Ile Asp Asp Arg Arg Ser Ala Ala Leu Ser Leu
        275                 280                 285

Leu Gly Ser Leu Asn Met Leu Leu Thr Ser Asp Glu Gly Arg Glu Tyr
    290                 295                 300
```

```
Thr Pro Ala Glu Cys Val Arg Trp Leu Ser Asp Ala Gly Phe Thr Asp
305                 310                 315                 320

Val Arg Thr Thr Ala Val Ser Gly Pro Asp Thr Leu Ala Ile Gly Arg
                325                 330                 335

Lys Pro Arg

<210> SEQ ID NO 27
<211> LENGTH: 20
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: S =C or G; Y=C or T; B =C, G or T and N=A, T,
      C or G

<400> SEQUENCE: 27
tsgcstgctt cgaygcsatc                                              20

<210> SEQ ID NO 28
<211> LENGTH: 20
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: =C or G; Y=C or T; B =C, G or T and N=A, T, C
      or G
<220> FEATURE:
<221> NAME/KEY: misc_feature
<222> LOCATION: (6)..(6)
<223> OTHER INFORMATION: n is a, c, g, or t

<400> SEQUENCE: 28
tggaanccgc cgaabccgct                                              20

<210> SEQ ID NO 29
<211> LENGTH: 19
<212> TYPE: DNA
<213> ORGANISM: Artificial Sequence
<220> FEATURE:
<223> OTHER INFORMATION: forward primer

<400> SEQUENCE: 29
ctgcagccac ggctactac                                               19

<210> SEQ ID NO 30
<211> LENGTH: 20
<212> TYPE: DNA
<213> ORGANISM: Artificial Sequence
<220> FEATURE:
<223> OTHER INFORMATION: reverse primer

<400> SEQUENCE: 30
gctcgtaggt cttggtcgag                                              20

<210> SEQ ID NO 31
<211> LENGTH: 18
<212> TYPE: DNA
<213> ORGANISM: Artificial Sequence
<220> FEATURE:
<223> OTHER INFORMATION: forward primer

<400> SEQUENCE: 31
gtgggccgac tcgaagag                                                18
```

```
<210> SEQ ID NO 32
<211> LENGTH: 20
<212> TYPE: DNA
<213> ORGANISM: Artificial Sequence
<220> FEATURE:
<223> OTHER INFORMATION: reverse primer

<400> SEQUENCE: 32
ggttgaccag atcgtcggta                                              20

<210> SEQ ID NO 33
<211> LENGTH: 20
<212> TYPE: PRT
<213> ORGANISM: Amycolatopsis sulphurea

<400> SEQUENCE: 33

Gly Pro Val Gly Leu Val Ser Thr Gly Cys Thr Ser Gly Val Asp Val
1               5                   10                  15

Ile Gly His Ala
            20

<210> SEQ ID NO 34
<211> LENGTH: 24
<212> TYPE: PRT
<213> ORGANISM: Amycolatopsis sulphurea

<400> SEQUENCE: 34

Val Pro Val Ser Ser Ile Lys Ser Met Val Gly His Ser Leu Gly Ala
1               5                   10                  15

Ile Gly Ser Leu Glu Val Ala Ala
            20

<210> SEQ ID NO 35
<211> LENGTH: 9
<212> TYPE: PRT
<213> ORGANISM: Amycolatopsis sulphurea

<400> SEQUENCE: 35

Val Ser Glu Gln Ala Gly Gly Leu Asp
1               5

<210> SEQ ID NO 36
<211> LENGTH: 6
<212> TYPE: PRT
<213> ORGANISM: Amycolatopsis sulphurea

<400> SEQUENCE: 36

Leu Gly Tyr Asp Ser Leu
1               5

<210> SEQ ID NO 37
<211> LENGTH: 7
<212> TYPE: PRT
<213> ORGANISM: Artificial Sequence
<220> FEATURE:
<223> OTHER INFORMATION: methyltransferase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
```

<223> OTHER INFORMATION: Xaa can be any naturally occurring amino acid

<400> SEQUENCE: 37

Glx Xaa Gly Xaa Gly Xaa Gly
1               5

<210> SEQ ID NO 38
<211> LENGTH: 6
<212> TYPE: PRT
<213> ORGANISM: Artificial Sequence
<220> FEATURE:
<223> OTHER INFORMATION: conserved domain
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 38

Gly Xaa Gly Xaa Xaa Ala
1               5

<210> SEQ ID NO 39
<211> LENGTH: 18
<212> TYPE: PRT
<213> ORGANISM: Artificial Sequence
<220> FEATURE:
<223> OTHER INFORMATION: conserved domain
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid

<400> SEQUENCE: 39

Gly Xaa Xaa Xaa Gly Xaa Gly Xaa Xaa Xaa Ala Xaa Xaa Xaa Xaa Xaa
1               5                   10                  15

Xaa Gly

<210> SEQ ID NO 40
<211> LENGTH: 17
<212> TYPE: PRT
<213> ORGANISM: Artificial Sequence
<220> FEATURE:
<223> OTHER INFORMATION: conserved domain
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature

```
<222> LOCATION: (11)..(16)
<223> OTHER INFORMATION: Xaa can be any naturally occurring amino acid

<400> SEQUENCE: 40

Gly Xaa Gly Xaa Xaa Gly Xaa Xaa Xaa Ala Xaa Xaa Xaa Xaa Xaa Xaa
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: conserved domain
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(16)
<223> OTHER INFORMATION: Xaa can be any naturally occurring amino acid

<400> SEQUENCE: 41

Gly Xaa Gly Xaa Xaa Gly Xaa Xaa Xaa Ala Xaa Xaa Xaa Xaa Xaa Xaa
1               5                   10                  15

Gly

<210> SEQ ID NO 42
<211> LENGTH: 26
<212> TYPE: DNA
<213> ORGANISM: Artificial Sequence
<220> FEATURE:
<223> OTHER INFORMATION: forward primer

<400> SEQUENCE: 42
gaattcccac cgtccacata ggaaag                                      26

<210> SEQ ID NO 43
<211> LENGTH: 28
<212> TYPE: DNA
<213> ORGANISM: Artificial Sequence
<220> FEATURE:
<223> OTHER INFORMATION: reverse primer

<400> SEQUENCE: 43
gacgtcgtga tgatcaccaa tgtgctgc                                    28

<210> SEQ ID NO 44
<211> LENGTH: 22
<212> TYPE: DNA
<213> ORGANISM: Artificial Sequence
<220> FEATURE:
<223> OTHER INFORMATION: forward primer

<400> SEQUENCE: 44
ggcgcccagc ttcaacgacg gc                                          22

<210> SEQ ID NO 45
<211> LENGTH: 25
```

```
<212> TYPE: DNA
<213> ORGANISM: Artificial Sequence
<220> FEATURE:
<223> OTHER INFORMATION: reverse primer

<400> SEQUENCE: 45
gaattccgac ctcagcgtcc acatc                                      25
```

GENES FOR BIOSYNTHESIS OF TETRACYCLINE COMPOUNDS AND USES THEREOF

FIELD OF THE INVENTION

This invention relates to genetically engineered cells, and to proteins and genes useful in the production of tetracycline compounds, to methods of producing tetracycline compounds, and to tetracyclines thereby produced. The present invention is based on the cloning and heterologous expression of genes encoding the chelocardin biosynthetic pathway.

BACKGROUND OF THE INVENTION

Tetracyclines are a large group of drugs with a common basic structure consisting of four linearly fused six-membered rings. Chlortetracycline isolated from *Streptomyces aureofaciens* was introduced in 1948 and oxytetracycline, derived from *Streptomyces rinosus*, was introduced in 1950 (Projan et al., 2006. SIM News 55, 52-60). Tetracycline and 6-demethyl-7-chlortetracycline (demethylchlortetracycline), both produced by *Streptomyces aureofaciens*, are two additional tetracycline compounds produced by fermentation process. A number of semi-synthetic tetracyclines generated by chemical modification of tetracycline or demeclocycline and with improved pharmacological properties, have been generated over the years such as methacycline, doxycycline and minocycline. Recently, a novel semisynthetic analogue, tigecyclin, derived from minocycline has been licensed for treatment of bacterial infections (Chopra et al., Roberts M. 2001. Microbiol Mol Biol Rev; 65:232-260). Tetracyclines were the first broad-spectrum antibiotics. They are effective against a variety of microorganisms and are thus often used indiscriminately. Tetracyclines bind reversibly to the 30S subunit of the bacterial ribosome in a position that blocks the binding of the aminoacyl-tRNA to the acceptor site on the mRNA-ribosome complex. They are bacteriostatic for many gram positive and gram negative bacteria, including some anaerobes, for *rickettsiae, chlamidiae, mycoplasmas* and L-forms, and for some protozoan parasites. The widespread use of tetracyclines has led to the emergence of resistance even among highly susceptible species such as pneumococci and group A streptococci. For this reason a novel antibacterial is needed; tetracyclines, as relatively safe antibiotics, still represent potentially useful candidates for antibacterial drug discovery programmes. The tetracycline analogue doxycycline has been used for decades for the inhibition of the malaria-causing *Plasmodium falciparum*. Novel tetracycline (TC) analogues have been developed in the past (Projan et al., 2006. SIM News 55, 52-60). A small group of TC analogues, of which the primary target is not a bacterial ribosome, such as chelocardin and 6-thiatetracycline, have been isolated or synthesised (Chopra I. 2004. Antimicrob Agents Chemother; 38(4):637-40).

This small group of TC analogues are bactericidal, rather than bacteriostatic. Their mode of action is clearly not oriented towards a bacterial ribosome. It is believed that the primary target of these small group of tetracycline analogues, such as chelocardin, is the bacterial cytoplasmic membrane, hence the activity of these compounds against tetracycline resistant strains. This has been suggested in the study by Olivia et al. (1992, Antimicrob Agents Chemother. 36(5): 913-919), in which the activities of these tetracycline analogues were examined against *E. coli* and *Staphylococcus aureus* strains containing determinants for efflux Tet(B) and Tet(K) or ribosomal protection Tet(M). Chopra et al. (2001, Curr Opin Pharmacol. 1(5):464-9) have demonstrated that Tet(B) and Tet(M) determinants in E. coli or *Staphylococcus aureus* offer little or no protection against the tetracycline analogues chelocardin and 6-thiatetracycline, thus representing an interesting antibacterial activity. Unfortunately, the clinical trials conducted with one of these atypical TCs (6-thiatetracycline) have revealed adverse side-effects. LD50 of both, 6-thiatetracycline and chelocardin, obtained in acute toxicity studies in mice, are considerably lower that those obtained by classical TCs, possibly reflecting the membrane-disruptive properties of atypical TCs. In view of this potential mode of action it is not surprising that the atypical TCs exhibit activity against TC-resistant strains. Therefore, the use of atypical TCs (such as chelocardin) can not be considered because of their potential for causing side effects. Selected tetracycline analogues have also displayed potent antifungal activity. Several chemically modified tetracycline analogues (CMTs), which were chemically modified to eliminate their antibacterial efficacy, such as CMT3, were found to have potent antifungal properties (Liu et al., 2002, Antimicrob agents chemother 46, 1447-1454).

Tetracycline analogues, including the medically important tetracycline analogues, show other, non-antibacterial pharmacological properties, therefore showing useful activity for the treatment of chronic neurodegenerative diseases (Parkinson's, Huntington's) and autoimmune condition multiple sclerosis (Domercq and Matute, 2004, Trends Pharmacol Sci. 2004. 25(12):609-12, Brundula et al., 2002, Brain 125: 1297-308). In addition, some of the TCs inhibit the activity of matrix metalloproteinases (MMPs), which play an important role in the development of atherosclerosis, rheumatoid arthritis, osteoporosis, tumour invasion and metastasis (cancer development/progression) (Fife et al., 2000, Cancer Lett. 29; 153(1-2):75-8). Pathologies that are responsive to tetracycline compounds include inflammatory process-associated states. The term "inflammatory process-associated state" includes states involving inflammation or inflammatory factors such as MMPs.

Some of these MMPs break down fibrillar collagens and are known as collagenases (e.g. MMP-1, MMP-8 and MMP-13), some can affect basement membrane collagen (collagen IV) and are known as gelatinases (MMP-2 and MMP-9). Tetracycline analogues can inhibit both collagenases and gelatinases (Peterson J. T. 2004, Heart Fail Rev., 9, 63-79). MMPs-degrading enzymes (e.g. MMP-8, MMP-9), present in the intracellular matrix of tissue facilitate angiogenesis by allowing new blood vessels to penetrate into the matrix. Currently only Periostat® (CollaGenex Pharmaceuticals Inc.), also known as doxycycline, is approved for treatment of adult peridontitis, as an MMP inhibitor. The anti-angiogenic effect of tetracyclines may have therapeutic implications in inflammatory processes accompanied by new blood vessel formation, as it is the case in some stages of autoimmune disorders and cancer invasion. Metastat (Col-3), for example, has demonstrated good results in the treatment of Karposi's sarcoma (Phase II, Dezube et al., 2006, J Clin Oncol. 24(9):1389-94). TCs can also influence bone metabolism. Prophylactic administration of doxycycline reduces the severity of canine osteoarthritis in the dog anterior cruciate model (Yu et al., 1992. Arthritis Rheum. 1992 October; 35(10):1150-9). In a recent experiment it was demonstrated that minocycline, by stimulating new bone formation, prevents the decrease in mineral density (osteoporosis) observed in ovariestomized old rats (Wiliams et al., 1998. Adv Dent Res. 1998 November; 12(2):71-5), suggesting the potential use of TCs in the treatment of osteoporosis. Nevertheless, tetracyclines have been shown to demonstrate anti-inflammatory properties, antiviral properties and immunosuppressive properties. The tetracycline analogue minocycline, for example, is considered as a safe effective treatment for patients with mild to moderate rheumatoid arthritis. Tilley et al. 1995 (Ann Intern Med., 122, 2. 1995, 81-89.) carried out a clinical trial in which 109 patients on minocycline were compared to 110 patients on placebo. There was a significant improvement in joint swelling in the treated patients versus the placebo group and also improvement in joint tenderness, with no serious toxicity.

To date, all clinically useful TC antibiotics are either natural products, semisynthetic analogues, or chemically modified molecules, composed of four rings, designated A, B, C, and D (FIG. 1). The recently established crystal structure of tetracycline (TC)-bound 30s subunit (Brodersen et al., 2000, Cell, 103:1143-54.) has revealed that the side of the four-member ring structure of TC molecule, including carbons C1 to C3 and C10 to C12 ("south" and "east" side) interact significantly with the ribosome. Most semisynthetic tetracycline analogues with superior antibacterial activity, such as doxycycline, minocycline and the latest derivative tigecycline, have been modified at the "north-west" side of the tetracycline structure, covering carbons C4 to C9, which is in line with the structure-activity (SAR) results (Brodersen et al., 2000, Cell, 103:1143-54). The structure of chelocardin, in particular, differs from existing biosynthetically-derived natural tetracyclines, thus allowing novel chemistry to be carried out on the tetracycline backbone of chelocardin or modified matrices generated by biosynthetic-engineering approaches, which is the main scope of the invention. Combined synthetic and biosynthetic complementary strategies for novel TC compounds can be applied. The four ring naphtacene nucleus structure of chelocardin and a complex series of oxygen functional groups on the "south" side of the molecule fulfill the minimal structural requirements for bioactivity against both bacterial and mammalian targets. However, the structure of chelocardin is extremely non-polar, compared to other biosynthetic TC derivatives, which is a consequence of the lack of hydroxyl groups at positions C5 and C6, and the replacement of the amino group of the amide moiety at the position C2 with acyl. An addition, the methyl-group at the position C9 further enhances the non-polar properties of chelocardin at the same time altering/broadening the spectrum of biological targets, not only limited to bacterial cells. On the other hand, the free amino-group, not found "unprotected" in other natural tetracycline analogues introduces a degree of polarity. At the same time, it is one of the most useful functional groups that can be readily derivatized by a chemical synthesis approach, introducing changes in solubility, lipophilicity and new binding affinities into the molecule.

In the past, extensive data on the structure-activity relationship of TCs have been generated, showing that the molecular structure and functionality of different TCs allows them to be "chemically promiscuous" and interact with many macromolecules, hence exerting a broad spectrum of pharmacological effects. The present invention is related to the generation of novel TC analogues based on chelocardin itself and/or chelocardin analogues generated by methods of biosynthetic engineering, biotransformation and/or semisynthetic approaches. A more detailed description of the present invention is provided herein below.

DESCRIPTION OF THE DRAWINGS

FIG. 6 shows preferred groups of enzymes of the invention, together with their respective biosynthetic products.

SUMMARY OF THE INVENTION

Figure 1:
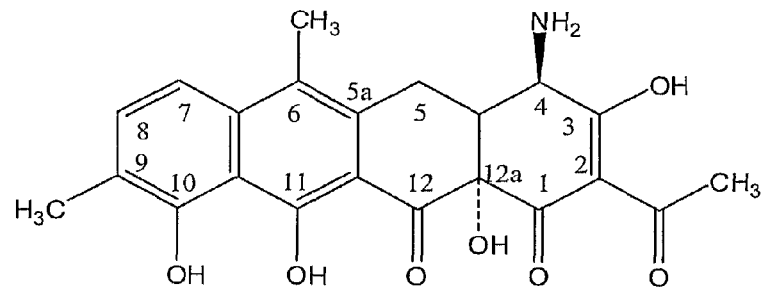
FIG. 1 shows the chemical structure of chelocardin.

The present invention relates to the application of biosynthetic engineering for the heterologous expression of an entire gene cluster for the biosynthesis of chelocardin or its analogues, either produced by *Amycolatopsis sulphurea* ATCC NRRL2822 or heterologously expressed in a surrogate host. The chelocardin gene cluster is cloned and can be expressed in a heterologous actinomycete host such as *Streptomyces lividans, Streptomyces albis, Streptomyces rimosus, Amycolatopsis orientalis* and *Nocardia* spp.

The present invention relates to processes and materials (including protein kits, DNA kits, nucleic acids, vectors and cells and cultures) for the heterologous expression of various Type-II polyketide gene clusters, such as the one involved in the biosynthesis of chelocardin. The present invention also relates to the preparation of novel substituted tetracycline compounds. The invention provides the entire nucleic acid sequence of the biosynthetic gene cluster for chelocardin production in *Amycolatopsis sulphurea*, and the use of all or part of the cloned DNA to produce novel chelocardin analogues in *Amycolatopsis sulphurea* or surrogate hosts. A previously unknown biosynthetic pathway for the biosynthesis of chelocardin was identified (see FIG. 3). New drug candidates can be obtained by the genetic manipulation of the discovered biosynthetic genes. Additional genes or inactivation of selected chelocardin-pathway encoding genes is used to modify the structure of the obtained tetracycline compound. Cells and nucleic acids of the invention can be used for the preparation of modified chelocardin molecules with alternative biological activities, such as antibacterial, antimalarial, antitumor, etc. agents.

Tetracycline compounds of the present invention are useful for treatment of bacterial and fungal infections, treatment of malaria, as a therapeutic in the treatment of inflammatory process-associated states such as cancer, periodontitis, osteoarthritis, rheumatoid arthritis, autoimmune condition multiple sclerosis and other pharmacological activities/pathologies such as cardiovascular and neurodegenerative disorders (Alzheimer's disease & Huntington's disease). The use of products produced by method of the current invention for the treatment of any of the medical indications stated above is also covered by the present invention.

The present invention also relates to a treatment for inhibiting microbial, fungal, antiviral and tumour growth, tumour invasion and metastasis, malaria causing protozoan parasites of the genus *Plasmodium*, and for a treatment of pathological conditions such as atherosclerosis, rheumatoid arthritis, multiple sclerosis, osteoporosis and useful activity for the treatment of chronic neurodegenerative diseases (Parkinson's, Huntington's). Chelocardin-derived matrices generated this way are useful for generating potential compounds or intermediates suitable for further modification by semi-synthetic or biotransformation approach. Designer tetracycline analogues can be applied using a rational approach by modifying the initiation module in the biosynthetic route in order to replace the methyl group of the acyl moiety at the position C2 with an amino group, thus resulting in an amide moiety. A number of positions on the chelocardin skeleton, such as positions C3, C4, C5, C6, C7, C8 and C9 can likely be modified using a rational or a combinatorial biosynthetic approach as well as a biotransformation approach, in order to produce novel TC-matrices, suitable substrates for further chemical modifications. Using combined approaches, biosynthetic and synthetic approaches, numerous chelocardin tetracycline analogues, with potential novel activity can be generated.

Figure 5:
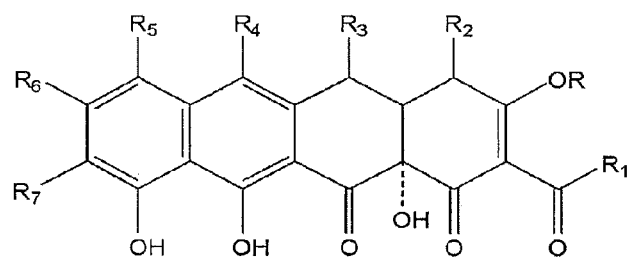
FIG. 5 shows a generic tetracycline structure based on the chelocardin tetracycline backbone.

By applying biosynthetic engineering approach designated positions (R1-R7 and OR; FIG. 5) can be modified by manipulation of DNA sequence encoding chelocardin biosynthesis and its co-expression with heterologous-genes from other tetracycline and more widely aromatic-polyketide (Type II) PKS gene clusters such as oxytetracycline, chlortetracycline, tetracenomycin, and others.

Figure 3:
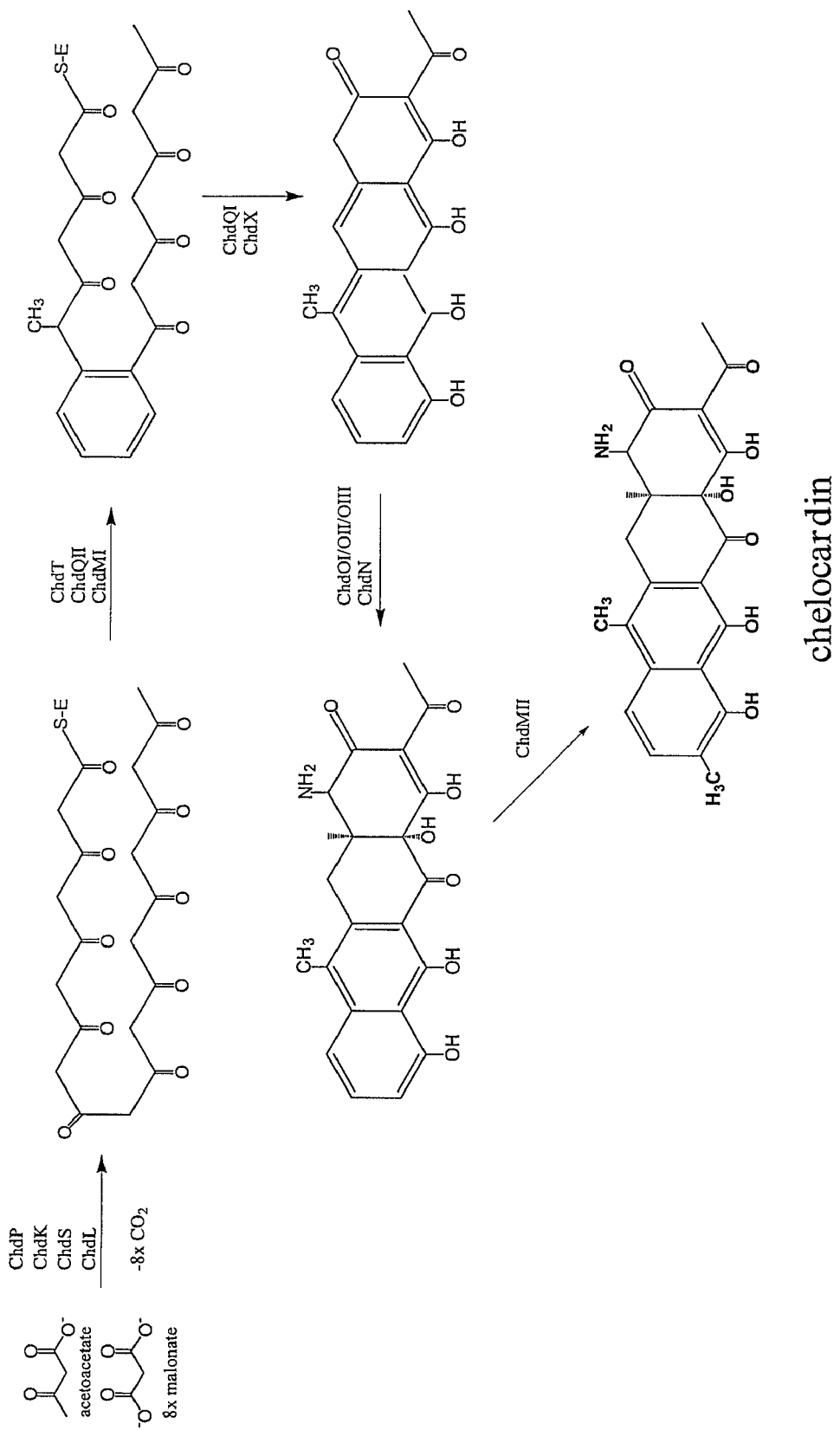
FIG. 3 shows the chelocardin biosynthesis pathway, according to the invention.

The chelocardin biosynthetic pathway according to the invention is shown in FIG. 3. The polyketide skeleton of chelocardin is assembled from an acetoacetate starter unit to which 8 malonate-derived acetate building blocks are attached by the action of the minimal PKS, namely ChdP, ChdK, ChdS. The polyketide chain is further subjected to methylation, C-9 ketoreduction, and cyclisation/aromatisation, by the action of the ChdMI methyltransferase gene, the ChdT ketoreductase, and the ChdQII cyclase/aromatase, respectively. After the cyclisation/aromatisation is completed by ChdQI and ChdX, the nascent aromatic compound is subjected to post-PKS reactions, i.e. oxidations, C-4 amination, and C-9 methylation, catalysed by three oxygenases ChdOI/ChdOII/ChdOIII, aminotransferase ChdN, and methyltransferase ChdMII, respectively.

culated by the NCBI/BLAST (blastx or blastp) algorithm using the default parameters as set by the NCBI (Altschul et al., 1990, *J Mol Biol*, 215, 403-10).

"Stringent conditions", within the meaning of the invention, shall be understood as being the stringent conditions as set forth according to Sambrook et al. ($2^{nd}$ ed., 1989, Cold Spring Harbor Laboratory Press, Cold Spring Harbor, N.Y.)

A "tetracycline compound" according to the invention is a compound having the chemical structure shown in FIG. 5, with R1-R7 and OR being arbitrary substituents. Preferred tetracyclines of the inventions are those specifically disclosed herein.

A "genetically engineered cell", within the meaning of the invention, is a cell which is modified by purposeful application of recombinant DNA technology to provide said cell with modified biochemical properties.

A "genetically engineered biosynthetic pathway", within the meaning of the invention, is a biosynthetic pathway which is modified by purposeful application of recombinant DNA technology, wherein said purposeful application of recombinant DNA technology involves addition of further genes/proteins/reactions to the pathway, and/or the deletion or inactivation of genes/proteins/reactions from the pathway, in order to obtain a modified biosynthetic pathway having improved performance or a modified biosynthetic pathway product.

A "catalytic function" of a polypeptide is understood to be the ability of said polypeptide to catalyse a certain biochemical reaction, or biological process.

A "gene cluster", within the meaning of the invention, shall be understood to be a totality of DNA coding for polypeptides required to catalyse a certain biochemical pathway. A gene cluster can be on a single DNA molecule, or can be on multiple DNA molecules, e.g. in form of a DNA library.

The present invention relates to a genetically engineered cell,

TABLE 1

Genes of the Chelocardin Gene Cluster

| SEQ ID NO: | Gene Name | Gene Function | Start | Stop | Length (bp) | Length (AA) | Start Codon | Stop Codon |
|---|---|---|---|---|---|---|---|---|
| 1 | chdP | Ketosynthase-alpha | 85 | 1384 | 1299 | 433 | GTG | TGA |
| 2 | chdK | Ketosynthase-beta | 1408 | 2635 | 1227 | 409 | GTG | TGA |
| 3 | chdS | Acyl Carrier Protein | 2662 | 2926 | 264 | 88 | ATG | TGA |
| 4 | chdQI | Cyclase | 3879 | 2973 | 906 | 302 | ATG | TGA |
| 5 | chdQII | Cyclase Aromatase | 17617 | 18562 | 945 | 315 | ATG | TGA |
| 6 | chdX | Cyclase/Aromatase | 16635 | 16183 | 453 | 151 | ATG | TGA |
| 7 | chdL | Acyl-CoA Ligase | 15753 | | | | GTG | |
| 8 | chdT | Ketoreductase | 16800 | 17589 | 789 | 263 | ATG | TGA |
| 9 | chdOI | Oxygenase | 11901 | 13113 | 1212 | 404 | ATG | TGA |
| 10 | chdOII | Oxygenase | 18530 | 19820 | 1290 | 430 | ATG | TGA |
| 11 | chdOIII | Oxygenase | 14436 | 14229 | 207 | 69 | ATG | TAG |
| 12 | chdMI | Methyltransferase | 14149 | 13126 | 1023 | 341 | ATG | TGA |
| 13 | chdMII | Methyltransferase | 4975 | 3970 | 1005 | 335 | GTG | TGA |
| 14 | chdN | Aminotransferase | 11724 | 10425 | 1299 | 433 | GTG | TGA |
| 15 | chdGIV | Glycosyltransferase | 5162 | 6359 | 1197 | 399 | ATG | TGA |
| 16 | chdTn | Transposase | 6584 | 8099 | 1515 | 505 | ATG | TGA |
| 17 | chdR | Exporter | 9686 | 8243 | 1443 | 481 | ATG | TGA |
| 18 | chdA | Transcriptional Regulator | 9836 | 10406 | 570 | 190 | GTG | TAA |

DETAILED DESCRIPTION OF THE INVENTION

"% identity", within the context of the present invention shall be understood the % identity of two sequences as calsaid cell being capable of producing a tetracycline compound, said tetracycline being produced by said cell by a genetically engineered biosynthetic pathway, wherein said genetically engineered biosynthetic pathway includes at least one reaction catalysed by a polypeptide selected from the group consisting of:

(a) a polypeptide of the chelocardin biosynthetic pathway, said polypeptide having the sequence of any of SEQ ID NO: 1 to 18;

(b) a polypeptide which is at least 80%, 90%, 95%, 99%, 99.9%, or 100% identical to a polypeptide of (a), wherein said polypeptide being 80%, 90%, 95%, 99%, 99.9%, or 100% identical has the same catalytic function as said polypeptide of (a).

This genetically engineered cell is thus purposefully engineered to provide a modified tetracycline biosynthetic pathway, which pathway includes at least one of the previously unknown genes of the chelocardin biosynthetic pathway provided by the present invention. Engineered cells of the invention may comprise a single one of the newly found genes or proteins of the chelocardin biosynthetic pathway, or they may include multiple or all of said newly found genes or proteins of the chelocardin biosynthetic pathway (SEQ ID NO:1 to 18). The person skilled in the art appreciates that any one of the genes or proteins of the present invention can be substituted or replaced by homologous genes, if these genes show the same catalytic function. Genetically engineered cells comprising such homologous genes or polypeptides are thus also an aspect of the invention.

The invention further relates to a genetically engineered cell as described above, wherein said genetically engineered biosynthetic pathway of said cell further includes at least one reaction catalysed by a polypeptide selected from the group consisting of (c) a polypeptide of any of SEQ ID NO: 19 to 26;

(d) polypeptide which is at least 80%, 90%, 95%, 99%, 99.9%, or 100% identical to a polypeptide of any of SEQ ID NO:19 to 26, wherein said polypeptide being 80%, 90%, 95%, 99%, 99.9%, or 100% identical has the same catalytic function as said polypeptide of SEQ ID NO:19-26.

Polypeptides of SEQ ID NO:19-26 are previously known enzymes the catalytic function of which can advantageously be applied in genetically engineered cells of the above described type. Notably, addition of these polypeptides allows to produce modified tetracycline compounds, such as e.g. the structures shown in the present application denoted Structure 1 to Structure 10, below.

The present invention further relates to a genetically engineered cell of the above kind, wherein said genetically engineered biosynthetic pathway of said cell includes all reactions catalysed by a polypeptide of a group consisting of (c) a polypeptide of any of SEQ ID NO:1 to 8;

(d) polypeptide which is at least 80%, 90%, 95%, 99%, 99.9%, or 100% identical to a polypeptide of any of SEQ ID NO:1 to 8, wherein said polypeptide being 80%, 90%, 95%, 99%, 99.9%, or 100% identical has the same catalytic function as said polypeptide of SEQ ID NO:1-8.

Polypeptides according to SEQ ID NO: 1-8 represent a minimum set of proteins capable of producing the core tetracycline compound shown as Structure 10. Genetically engineered cells of this type can also be used as a starting point for the purposeful manipulation of such cells, to produce modified tetracycline compounds.

The present invention also relates to a polypeptide selected from the group consisting of:

(a) a polypeptide of the chelocardin biosynthetic pathway, said polypeptide having the sequence of any of SEQ ID NO:1 to 18;

(b) a polypeptide which is at least 80%, 90%, 95%, 99%, 99.9%, or 100% identical to a polypeptide of the chelocardin biosynthetic pathway having a sequence of any of SEQ ID NO:1 to 18, wherein said polypeptide being 80%, 90%, 95%, 99%, 99.9%, or 100% identical has the same catalytic function as said polypeptide of the chelocardin biosynthetic pathway.

Such polypeptides of the chelocardin biosynthetic pathway are not previously not known. They can be used, individually or in combination, for the creation of new genetically engineered cells having modified tetracycline biosynthetic pathways, thus producing useful tetracycline compounds. In particular, they are useful for producing genetically engineered cells of the above described kind.

The present invention also relates to a nucleic acid encoding a polypeptide of the above described kind. Such nucleic acid can be in form of a single DNA molecule, or can be in form of multiple DNA molecules, or can be in form of a gene library, or can be in form of a plasmid, or in form of multiple plasmids. Such nucleic acid can be in isolated form, or can be recombinant DNA.

The present invention also relates to an entire gene cluster encoding a tetracycline biosynthetic pathway, said gene cluster comprising nucleic acid coding for (a) polypeptides according to each one of SEQ ID NO: 1 to 8, or (b) polypeptides which are at least 80%, 90%, 95%, 99%, 99.9%, or 100% identical to each one of SEQ ID NO:1 to 8, wherein said polypeptides being 80%, 90%, 95%, 99%, 99.9%, or 100% identical have the same catalytic function as said polypeptides of SEQ ID NO:1 to 8.

Said gene cluster in preferably in isolated form.

The present invention further relates to a gene cluster of the above described kind, said gene cluster further comprising nucleic acid coding for a polypeptide selected from the group consisting of:

(c) polypeptides according to SEQ ID NO:9 to 18, and (d) polypeptides which are at least 80%, 90%, 95%, 99%, 99.9%, or 100% identical to SEQ ID NO:9 to 18, wherein said polypeptide being 80%, 90%, 95%, 99%, 99.9%, or 100% identical have the same catalytic function as said polypeptides of SEQ ID NO:9 to 18.

The present invention further relates to a method for the biosynthetic production of a tetracycline compound, said method comprising the steps of providing a genetically engineered cell of the above described kind, providing a substrate compound, incubating said substrate compound with said genetically engineered cell under permissible conditions, and obtaining said tetracycline compound.

The present invention further relates to a tetracycline compound produced by this method.

The present invention further relates to a tetracycline compound of the above described kind, wherein said compound has a structure selected from the group consisting of

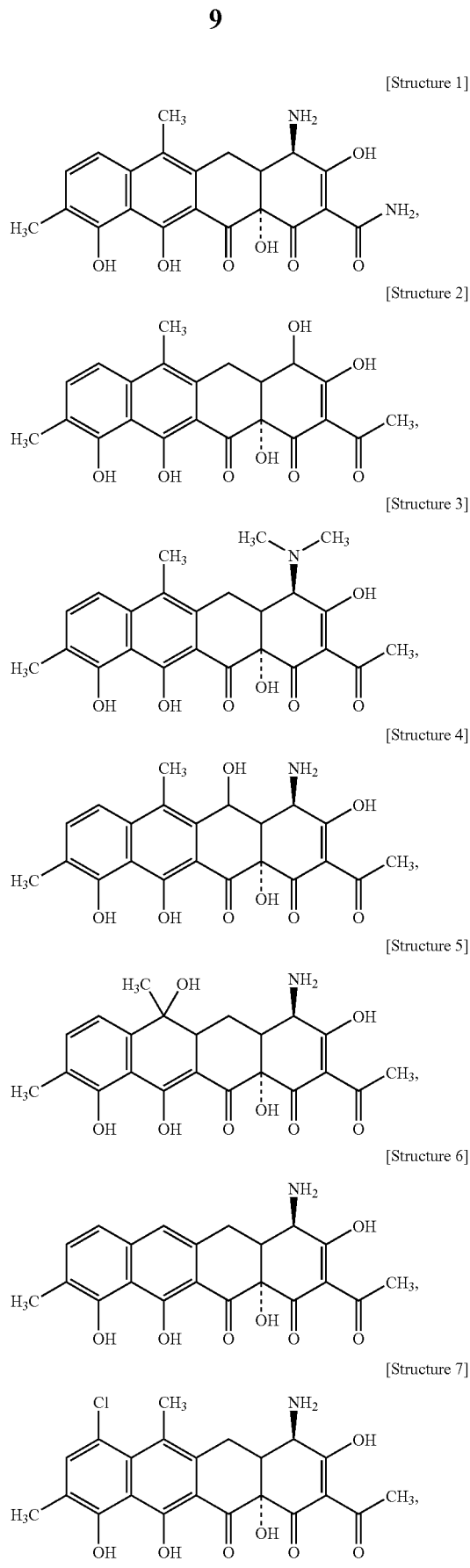

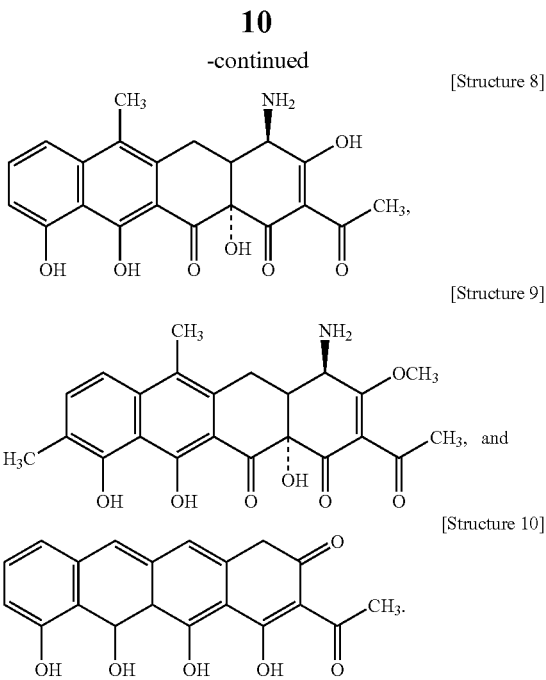

The present invention also relates to the individual compounds of Structure 1 to Structure 10.

It will be understood by the person skilled in the art that the exact position of double bonds in the above structures is cannot not always be exactly defined, due to spontaneous chemical rearrangement and/or possible tautomeric forms/isomers which can also influence the oxidative states of hydroxyl and keto groups at carbons 10, 11, 12 and carbon 1. It is understood that reference to the above structures, within the context of the present application, also refers to their tautomeric forms and isoforms, as explained above.

The present invention also relates to the use of these compounds for the treatment of bacterial or fungal infections, treatment of malaria, a neurodegenerative disease, Parkinson's disease, Huntington's, disease, periodontitis, an autoimmune condition, multiple sclerosis, atherosclerosis, rheumatoid arthritis, osteoporosis, tumour invasion, cancer and inflammatory states.

The present invention further relates to the use of a genetically engineered cell of the above described kind for the production of a medicament for treatment of bacterial or fungal infections, treatment of malaria, a neurodegenerative disease, Parkinson's disease, Huntington's, disease, periodontitis, an autoimmune condition, multiple sclerosis, atherosclerosis, rheumatoid arthritis, osteoporosis, osteoarthritis, tumour invasion, cancer and inflammatory states.

Polypeptides of SEQ ID NO:9-11 are oxygenases and are used in the production of Structures 1-9 as set out in FIG. 6 in the present invention. At least one of these enzymes is preferably included in a genetically engineered cell of the invention.

Polypeptides of SEQ ID NO:12-15 are also present in the wild type chelocardin biosynthetic gene cluster, thus, they are naturally optimized to co-operate with proteins of SEQ ID NO:1-11. At least one of these enzymes is preferably included in a genetically engineered cell of the invention.

Polypeptides of SEQ ID NO:16-18 are enzymes not involved in the biosynthetic pathway, but supporting the functioning of the enzymes of the SEQ ID NO:1-8 in a cellular environment (e.g. by transporting metabolites across cell membranes, by providing resistance to the final product, by activation of protein expression, and by other favourable effects). At least one of these enzymes is preferably included in a genetically engineered cell of the invention.

Polypeptides of SEQ ID NO:19-26 are heterologous enzymes not comprised in the wild type chelocardin biosynthetic gene cluster. They can be use to design and construct further tetracycline structures with improved properties, as exemplified in FIG. 6 of the present application. At least one of these enzymes is preferably included in a genetically engineered cell of the invention.

The present invention also relates to the (previously unknown) proteins according to SEQ ID NO:1-18 as such, and to DNA molecules encoding the same.

Methods of the invention are preferably conducted in a bioreactor or in a fermenter.

In the accompanying sequence listing,
SEQ ID NO:1 codes for ChdP,
SEQ ID NO:2 codes for ChdK,
SEQ ID NO:3 codes for ChdS,
SEQ ID NO:4 codes for ChdQI,
SEQ ID NO:5 codes for ChdQII,
SEQ ID NO:6 codes for ChdX,
SEQ ID NO:7 codes for ChdL,
SEQ ID NO:8 codes for ChdT,
SEQ ID NO:9 codes for ChdOI,
SEQ ID NO:10 codes for ChdOII,
SEQ ID NO:11 codes for ChdOIII,
SEQ ID NO:12 codes for ChdMI,
SEQ ID NO:13 codes for ChdMII,
SEQ ID NO:14 codes for ChdN,
SEQ ID NO:15 codes for ChdGIV,
SEQ ID NO:16 codes for ChdTn,
SEQ ID NO:17 codes for ChdR,
SEQ ID NO:18 codes for ChdA,
SEQ ID NO:19 codes for OxyD,
SEQ ID NO:20 codes for OxyT,
SEQ ID NO:21 codes for OxyE,
SEQ ID NO:22 codes for OxyL,
SEQ ID NO:23 codes for OxyS,
SEQ ID NO:24 codes for OxyG
SEQ ID NO:25 codes for Cts4, and
SEQ ID NO:26 codes for TcmO.

Envisaged are further tetracycline compounds of FIG. 5 having the following substituents:
R1: $CH_3$ or $NH_2$ (otc homologue oxyD (Zhang et. al., 2006, Appl. Environ. Microbiol., 72(4):2573-2580); Zhang et al., 2007, J Biol Chem. 282(35):25727-25)
R2: $NH_2$ or OH. or $N(CH3)_2$ (inactivation of chdN or co-expression with oxyT (Zhang et. al., 2006, Appl. Environ. Microbiol., 72(4):2573-2580); Zhang et al., 2007, J Biol Chem. 282(35):25727-25)
R3: H or OH (otc co-expression with oxyE/oxL/oxyS/oxyG (Zhang et. al., 2006, Appl. Environ. Microbiol., 72(4):2573-2580); Zhang et al., 2007, J Biol Chem. 282(35):25727-25)
R4: $CH_3$ or H or/and OH (inactivation of chdMI or co-expression with oxyxE/oxyL/oxyS/(otcC)/oxyG (Peric-Concha et al., 2005, J. Biol. Chem.; 280(45):37455-60; Zhang et al., 2007, J Biol Chem. 282(35):25727-25).
R5: H or Cl (ctc co-expression with chl (cts4) (Dairi et al, 1995, Biosci. Biotechnol. Biochem. 59(6):1099-106))
R6: H
R7: $CH_3$ or H (inactivation of chdMII)
OR: OH or $OCH_3$

EXAMPLES

Example 1

Cloning of the Chelocardin Gene Cluster

The cloning the chelocardin cluster starts with isolating a PCR template DNA of a chelocardin producer, *Amycolatopsis sulphurea* (NRRL2822), followed by a PCR using degenerate primers based on universally conserved motifs of Type-II acyl-ketosynthase alpha (KSα) (Metsa-Ketela et al., 1999, FEMS Microbiol Lett.; 180(1):1-6). The partial KSα nucleotide sequence of the PCR product was confirmed by sequencing. The PCR product was used as a probe against BamHI, SacI, BgIII, SphI, EcoRI, and NcoI total restriction digests of *A. sulphurea* genomic DNA. An 8 kb EcoRI-fragment that gave a positive result after Southern hybridization with a DIG-labelled KSα PCR probe was the most suitable for generating a shotgun library in pUC19. A shotgun library of app. 8 kb EcoRI digests of *A. sulphurea* genomic DNA was created in pUC19. On the basis of colony hybridization with the KSα probe, the 8 kb E1-E2 insert (FIG. 4) was selected for sequencing.

Figure 4:
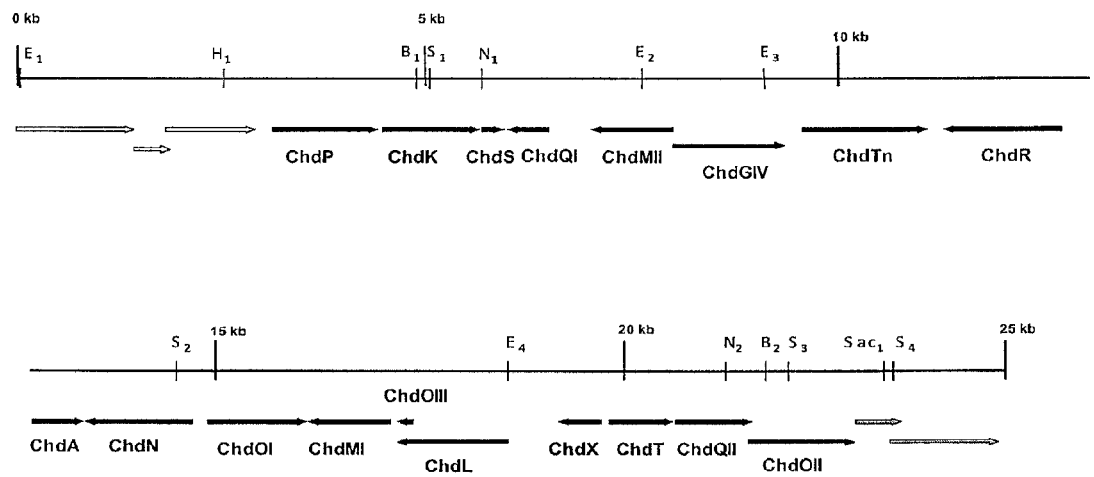
FIG. 4 shows the chelocardin biosynthetic gene cluster, and genes involved in chelocardin production. These are drawn as full arrows. The three genes on the left side of the cluster (white arrows) are involved in the B12 biosynthesis, coding for cobalamin biosynthesis protein, cobyric acid synthase 1 and cobyric acid synthase 2 (in order from left to right). On the right side of the chelocardin cluster genes (gray arrows), there are again several genes presumably not involved in the chelocardin biosynthesis. Restriction sites within the nucleotide sequence of the chelocardin cluster are marked as E=EcoRI, H=HindIII, B=BglII, S=SphI, N=NcoI, Sac=SacI, S3AI=Sau3AI.

The E1-E2 insert of the pLUC10E (FIG. 4) contains the genes clearly coding for a Type-II polyketide cluster, namely: KSα, KSβ, ACP, cyclase/aromatase, and mehyltransferase. Within that same insert, the genes involved in B12 vitamin biosynthesis were also found, namely cobyric acid synthase 1, cobyric acid synthase 2, and the cobalymin biosynthesis enzyme (FIG. 4).

Anticipating that the Type-II polyketide chelocardin cluster is less than 30 kb in size, a cosmid library was constructed in *E. coli* XL1-Blue MR from genomic DNA derived from a chelocardin producer, *Amycolatopsis sulphurea* (NRRL 2822). The cosmid library was screened by colony hybridization using a single KSα probe obtained by PCR using degenerated oligonucleotides, generated on the basis of conserved KSα nucleotide sequences (Metsa-Ketela et al., 1999, FEMS Microbiol Lett.; 180(1):1-6).

An integrative conjugative cosmid vector pLUS02 (FIG. 2) was first constructed as a tool to create a cosmid library and to speed up the subsequent conjugation and heterologous expression of the many positive clones, found by colony hybridization using a single probe.

The pLUS02 cosmid was used as the basis for the *Amycolatopsis sulphurea* genomic library. For constructing the pLUS02 (FIG. 2), the commercial SuperCos1 vector (Stratagene) that contains an *E. coli* origin of replication, a selectable drug resistance marker, and the cos sites of phage lambda was used. SuperCos1 itself cannot be transferred between *E. coli* and *Streptomyces*, and is unable to replicate in *Streptomyces*. To circumvent this deficit, SuperCos1 was upgraded with the insertion of the "oriT, attP, int" cassette. The oriT of an IncP transmissible plasmid promotes the transfer of DNA by conjugation from an *E. coli* donor strain to an *Streptomyces/Actinomyces* host recipient. The attP and the integrase from actinophage ΦC31 enable the site-specific integration of the conjugated DNA into the phage attachment site in a *Streptomyces* chromosome (Bierman et al., 1992, Gene 116: 43-49). Therefore, no additional subcloning is needed for heterologous expression after identifying the relevant cosmids within the cosmid library.

By upgrading the commercial SuperCos1 vector with the "oriT, attP, int" cassette, we created a vector pLUS02 that enables us to carry out faster and easier functional analyses of multiple cosmids. The cloning capacity of the 11.6 kb pLUS02 cosmid vector is 33.4 kb, which, together with other properties, renders this tool suitable for cloning and heterologous expression of the many Type-II polyketide clusters.

The pLUS02-based genomic library of Amycolatopsis sulphurea was screened for the presence of the chelocardin gene cluster using a Type-II PKS probe (KSα). Eighteen positive clones were selected out of 1600 colonies that were hybridized. At this point, additional PCR screening was performed using the primers based on the pLUC10E, selecting the clones that did not have a cobyric acid synthase 2 (left side of the chelocardin gene cluster, FIG. 4), while at the same time did contain a methyltransferase (ChdMII, FIG. 4). On the basis of the PCR screen and end-sequencing of the cosmids, the VII C4 cosmid was selected, sequenced, and roles of the gene products were determined in silico.

The genes involved in the biosynthesis of chelocardin have been heterologously expressed in different *Streptomyces* and non-streptomycete hosts. For the production, vegetative and production media, together with the method for extraction, were optimized for the strains.

An HPLC method was carried out to collect fractions of the extracts of the chosen host productive strains carrying the entire gene cluster encoding for chelocardin biosynthesis. Biological activities of the fractions were tested against *Micrococcus luteus*. The active fractions were subjected to further MS/MS analysis which confirmed the presence of a sodium adduct of chelocardin with a corresponding mass of m/z=413 and a proton adduct m/z=412.

Example 2

Isolation of Amycolatopsis Sulphurea Genomic DNA

A 10% innoculum of *Amycolatopsis sulphurea* NRRL 2822 strain was grown in 25 mL of Tryptone Soy Broth (Oxoid) at 30° C. for 24 h. The mycelium was washed two times in 25 ml of TES buffer (25 mM Tris-HCl, pH8; 50 mM EDTA, pH8; 0.3 M Sucrosis), resuspended in 5 mL of TES buffer supplemented with 4 mg/mL Lyzozyme (Sigma) and 100 µg/mL RNase (Sigma), and incubated at 37° C. for one hour. Then, 170 µL of 10% SDS was added, followed by the addition of 800 µL of 0.5 M EDTA (pH8) and 20 µL of Proteinase K (Sigma). After a 30 minute incubation at 37° C., 500 µL of 10% SDS was added. After one hour of incubation at 37° C., 3 mL of TE buffer (10 mM Tris-HCl, pH8; 1 mM EDTA, pH8), 2 mL of 5 M NaCl and 5 mL of TNE buffer (10 mM Tris-HCl, pH8; 100 mM NaCl, 1 mM EDTA, pH8) were added, followed by phenol/chloroform (1:1) extractions and ethanol precipitation. The DNA was eluted in 1 mL of TE buffer. The sufficient purity and size of DNA were assayed by gel electrophoresis.

Example 3

Generating a Probe to be Used in the Search for Chelocardin Gene Cluster

A homologous hybridization probe for screening *A. sulphurea* genomic DNA for chelocardin was generated by PCR using degenerated oligonucleotide primers. The primers were designed to amplify a fragment of Type-II ketosynthase alpha (KSα) gene (Metsa-Ketela et al., 1999, FEMS Microbiol Lett.; 180(1):1-6), namely: PKSF: 5'-TSGCSTGCTTC-GAYGCSATC-3' [SEQ ID NO: 27], and PKSR: 5'-TG-GAANCCGCCGAABCCGCT-3' [SEQ ID NO: 28], where S=C or G; Y=C or T; B=C, G or T and N=A, T, C or G.

The PCR conditions for the amplification of KS genes were as follows. About 10 ng of purified DNA template, 1 pmol of each primer, 0.5 mM dNTP, 10% DMSO, 1× Taq polymerase reaction buffer, 2 mM MgCl2, 1 µL Taq DNA Polymerase were used in the final reaction volume of 50 µL. The PCR reaction started with a longer denaturation phase (5'/95° C.) before adding Taq Polymerase. Thirty cycles were set as follows: denaturation (1'/95° C.), annealing (1'/64° C.) and extension (1.5'/72° C.). The reaction was ended with a longer final extension (10'/72° C.). The sequence analysis of the PCR products confirmed the KSα sequence. The products were DIG-labelled according to the kit manufacturer (Roche) and used as a probe for Southern hybridization.

Example 4

Southern Blots and DNA Hybridization

The DIG-labelled KSα PCR product was used for hybridization against the BamHI, SacI, BglII, SphI, EcoRI, and NcoI total restriction digests of *A. sulphurea* genomic DNA, separated by gel electrophoresis (0.8% gel, for 20 h at 25V). The DNA was transferred to the positively charged Hybond-N+ membrane (Amersham Pharmacia) according to the manufacturer.

Prehybridization and hybridization were performed at 46° C., then washed two times for 15 minutes in 2×SSC, 0.1% SDS at room temperature and two times for 5 minutes in 0.2×SSC, 0.1% SDS at 45° C. The approximately 8 kb EcoRI fragment proved to be the most suitable for creating a shotgun library.

Example 5

Generating a Shotgun Library

A high quality *A. sulphurea* genomic DNA was completely digested with the restriction endonuclease EcoRI and size fractionated by gel electrophoresis (1% agarose gel, 1.5 V/cm, 20 h). The separated DNA was excised from the gel in several layers, covering 6-10 kb fragments. Each layer of DNA was extracted from the gel using Wizard SV Gel and PCR Clean-Up System (Promega). A fraction of each isolate was run on a fresh gel (1% agarose, 5 V/cm, 2 h), transferred to a Hybond-N+ membrane (Amersham Pharmacia) and hybridized again using the same KSα probe to select for the samples with the highest concentration of the desired 8 kb fragment with the chelocardin cluster. The selected sample was used in a cloning reaction with a dephosporylated pUC19/EcoRI. The ligation mix was transformed into electrocompetent *E. coli* DH10β and the shotgun library was searched for the presence of genes from the chelocardin cluster by colony hybridization.

For colony hybridization, cells from single colonies after transformation were inoculated on a positively charged Hybond-N+ membrane (Amersham Pharmacia), placed on top of a layer of 2TY agar (Tryptone 16 g; Yeast extract 10 g; NaCl 5 g pH 7.0), supplemented with ampicillin (100 mg/L). After an overnight incubation at 37° C., the membrane with grown colonies was put sequentially on Whatman papers, soaked in
10% SDS for 5 minutes,
0.5 M NaOH; 1.5 M NaCl for 10 minutes
1.5 M NaCl; 0.5 M Tris-HCl (pH7.5) for 10 minutes
2×SSC for 10 minutes.

Then the membrane was washed in 2×SSC containing 200 µg/mL Proteinase K for approximately one hour. Colony debris was removed with a gloved finger. The membrane was briefly washed in 2×SSC, air-dried, and baked at 80° C. for 1-2 hours. Prehybridization and hybridization were performed at 42° C., then washed two times for 15 minutes in 2×SSC, 0.1% SDS and two times for 15 minutes in 0.2×SSC, 0.1% SDS, both at 68° C.

Six positive clones obtained from colony hybridization of an 8 kb EcoRI-EcoRI shotgun library were subjected to additional PCR analysis, confirming the presence of KSα, a Southern blot/DNA hybridization using a KSα probe, and end-sequencing of the inserts. One of the positive plasmids, pLUC10E, was chosen for sequencing by primer walking. The 8 kb EcoRI1-EcoRI2 insert revealed five open reading frames characteristic of the expected Type-II chelocardin gene cluster, namely: KSα, KSb, ACP, cyclase/aromatase, and mehyltransferase. As shown in FIG. 3A, the insert also contained 3 genes involved in vitamin B12 biosynthesis, namely cobyric acid synthase, the cobalymin biosynthesis enzyme, and the cobalbumin biosythesis enzyme. This characteristic of the insert shows that this is one end of the cluster, which was exploited as described later.

Example 6

Construction of a Conjugable Integrative Cosmid

Figure 2:
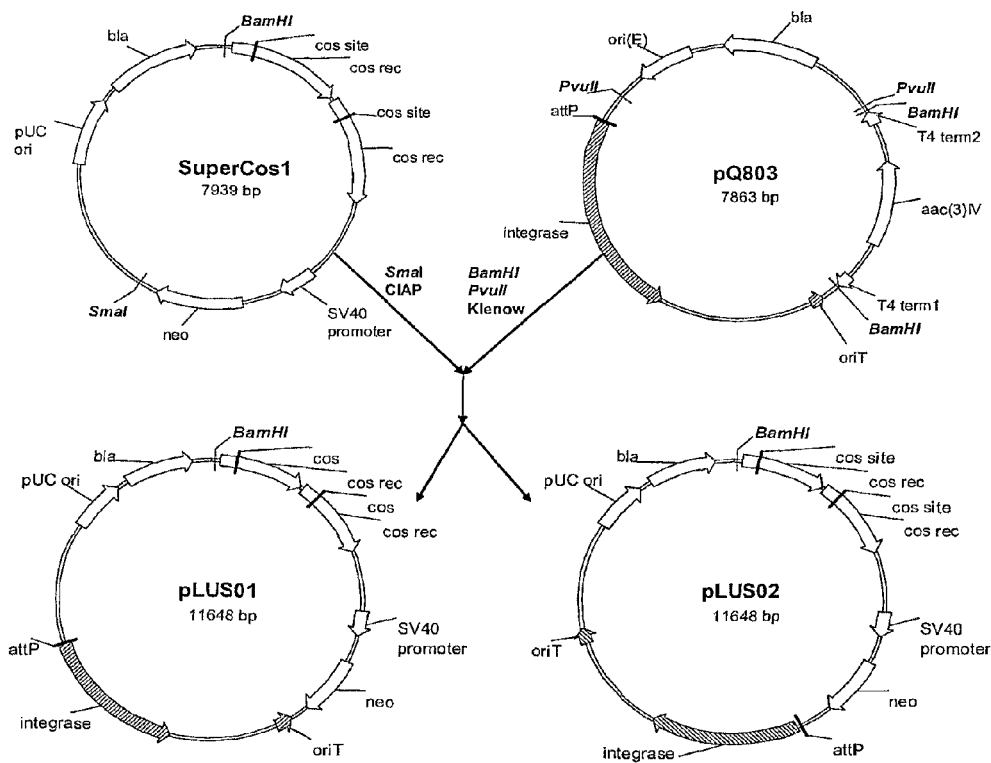
FIG. 2 shows the cloning of the pLUS02 cosmid used for constructing a genomic library of *A. sulphurea*.

The 3.7 kb PvuII-BamHI fragment containing the "oriT, attP, int" cassette from pQ803 (A. Almuteirie, PhD Thesis, 2006, University of Strathclyde) was blunt-ended by Klenow and subcloned into SmaI-linearized and dephosphorylated SuperCos1 (FIG. 2). The efficiency of conjugation of the two cosmids with different orientations of the "oriT, attP, int" cassette, namely pLUS01 and pLUS02, was compared. The conjugation efficiency was expressed as the ratio of exconjugants (*S. coelicolor* M145) per donor (*E. coli* ET12567/pUZ8002), both determined by the number of CFU. Repeatedly, the pLUS02 version of the cosmid conjugated at a higher frequency than the pLUS01 version. The pLUS02 cosmid yielded $1.5*10^{-6}$ exconjugants per recipient while the pLUS01 version conjugated at $7.2*10^{-6}$ exconjugants per recipient. Due to this small but consistent difference in conjugation efficiency, the pLUS02 cosmid was selected as tool for creating a genomic library of *Amycolatopsis sulphurea*.

Example 7

Cloning Packaging and Transduction

DNA isolation was carried out as described earlier (Example 1). *A. sulphurea* genomic DNA was partially digested with the restriction endonuclease Sau3AI. Optimal digestion conditions to generate large DNA fragments of app. 35 kb size range were empirically determined by conducting a series of digestions, followed by the appropriate scale-up. The DNA was size fractionated by gel electrophoresis, and cloned into the unique BamHI cloning site of a dephosphorylated pLUS02. The in vitro packaging of the ligation mix and the transduction of phage particles into the *E. coli* host XL1-BlueMR was done according to the Gigapack III Gold packaging kit supplier (Stratagene). The cosmid pLUS02 was used as a basic tool for the preparation of an *Amycolatopsis* sp. genomic library. The 11.6 kb pLUS02 cosmid vector contains the lambda cos site to promote packaging of vectors containing approximately 38 to 52 kb DNA fragments in total into phage particles. From the pLUS02-based *Amycolatopsis* sp. genomic library, 60 cosmids were isolated by an alkaline lysis procedure (Bimboim H C and Doly J. 1979. DNA Nucleic Acids Res. 7:1513-1523). All the cosmids (60 out of 60) within the bank contained an insert of sufficient size to fulfill the phage packaging capacity requirements. The 60 isolated cosmids were digested with EcoRI, the restriction fragments were separated by gel electrophoresis, and the sizes of the cosmids were determined by the Quantity One Gel Doc documentation system. All 60 isolated cosmids showed a highly representative different restriction pattern with an average size of 44.9 kb, which renders the cloning capacity of the vector 33.4 kb in average.

Example 8

Screening for the Chelocardin Cluster by Colony Hybridization

Within the library of 2400 clones, 1600 were screened by colony hybridization, as described previously. Cosmid DNA from approximately 1600 clones was spotted onto a Hybond-N+ membrane (Amersham Pharmacia) and hybridized with random-primed DIG-labelled strain-specific Type II PKS probe (KSa) by the following standard hybridization procedure (Roche). The membranes were prehybridized and hybridized as described.

A subset of 18 positive cosmids that were obtained on the basis of hybridization to the KSα probe was additionally screened via three PCRs. Degenerated KSα primers (Metsa-Ketela et al., 1999, FEMS Microbiol Lett.; 180(1):1-6), methyltransferase (from the chdMII gene, FIG. 4) primers (C-MT1F: 5'-CTGCAGCCACGGCTACTAC-3' [SEQ ID NO: 29], C-MT1R: 5'-GCTCGTAGGTCTTGGTCGAG-3') [SEQ ID NO: 30], and cobalbumin biosynthesis protein (FIG. 4) primers (CobdoF: 5'-GTGGGCCGACTCGAAGAG-3' [SEQ ID NO: 31], CobdoR: 5'-GGTTGACCAGATCGTCG-GTA-3') [SEQ ID NO: 32] were used in the following 50 μL reaction: 1×Pfu Polymerase buffer, 0.2 mM dNTPs, 4 μM forward- and reverse-primers, 5 μL od DMSO, 1 U of Pfu Polymerase, 1 μL of pLUC10E DNA. The PCR thermal cycles were set as follows: an initial cycle at 95° C. for 2 min, and 30 cycles at 95° C. for 30 s, 59.2° C.-61.5° C. for 30 s, and 72° C. for 2 min, followed by a final extension-cycle at 72° C. for 10 min. The strategy behind the PCR screen was to choose the cosmids that give the KSα and methyltransferase amplification products, but not the cobyric acid synthase product. Southern hybridization and end-sequencing of the selected inserts was also performed, and the VII C4 cosmid was chosen for sequencing.

Example 9

Identification of Gene Function in the Chelocardin Gene Cluster

The open reading frames (ORFs) were analysed with the FramePlot program and gene functions were assigned according to the homology searches in the protein database (BLASTp), supported with the conserved domain searches.

The isolated nucleic acid comprises the genes of the chelocardin gene cluster. As depicted in FIG. 4, the cluster contains 18 genes typical of a Type-II polyketide cluster. Consistently with the chelocardin structure, the cluster is comprised of three genes forming a "so-called" minimal Type-II PKS (KSα, KSβ, ACP), three genes involved in the cyclisation/aromatisation process, two genes for methyltransferases, one gene for aminotransferase, three genes for oxygenases, a gene for a ketoreductase, a gene for an acyl-CoA ligase, a gene for a drug resistance transporter and a transcriptional regulator, as well as a glycosyltransferase and a transposase which are redundant. A brief description of the genes involved in the biosynthesis of chelocardin follows:

ChdP-Acyl-Ketosynthase Alpha

BLASTp sequence analysis shows that the chdP sequence corresponds to a ketosynthase gene characteristic of Type-II PKS clusters. The tcsD keto-acylsynthase gene from the *S. auerofaciens* chlortetracycline gene cluster showed the highest similarity (77% identity) to the chdP gene. The oxyA gene from the oxytetracycline producer *S. rimosus* (76% identity), and the spiramycin producer *S. spiramyceticus* (71% identity) followed in homology. Together with these strains, many other (mostly Type-II) polyketide producers showed more than 70% identities, such as *S. echinatus* (aranciamycin), *S. albofaciens*, *S. platensis*, *S. fradiae* (urdamycin), *S. tendae* (cervimycin), *S. nogalater* (nogalamycin). The cmmP gene, coding for a ketosynthase in *S. griseus* subsp. *griseus* shows a 69% identity and is, according to Menendez et al. (2004, Chem Biol. 11(1):21-32) together with cmmK and cmmS, coding for a minimal PKS, responsible for the 20-C backbone of the glycosylated Type-II polyketide chromomycin. With the e-values ranging down to 4e-142, all BLASTp results strongly suggest that chdP is coding for a keto-acyl synthase alpha (KSα). The N terminal catalytic domain of the ChdP protein harbours a well conserved aa region around the highly conserved active site $Cys^{173}$ (GPVGLVSTGCTSGVD-VIGHA [SEQ ID NO: 33]) responsible for catalyzing the iterative condensation of the ketoacyl:ACP intermediates. In the C terminus of the protein there is an amino-acid sequence characteristic of the acyltransferase site (VPVSSIKSMVGH-SLGAIGSLEVAA [SEQ ID NO: 34]) with the active $Ser^{351}$ residue that binds to an acyl chain (Fernandez-Moreno et al., 1992. J Biol Chem. 267(27):19278-90).

ChdK-acyl-ketosynthase beta

According to BLASTp results, chdK is a keto-acyl synthase beta (KSβ), also named a chain length factor. Similarly as for KSα, *S. rimosus*, *S. aureofaciens*, *S. chartreusis*, *S. echinatus*, *S. antibioticus*, *S. argillaceus*, and *S. griseus* subsp. *griseus* return as hits with 73 to 63% aa identity. Ketosynthase domain active-site cysteine residue in ChdK is replaced by a highly conserved glutamine as in KSQ ($VSEQ^{181}AGGLD$ [SEQ ID NO: 35]) and in other chain-length factors of type II PKS synthases. According to Bisang et al. (1999, Nature 401, 502-505), the glutamine residue is important both for decarboxylase activity and for polyketide synthesis.

ChdS-acyl-carrier protein

The ChdS has the highest sequence similarity (59% identity) to *S. rimosus* acyl carrier protein (ACP), and harboures an active $Ser^{41}$ residue in the highly conserved motif (LGYDSL [SEQ ID NO: 36]), to which phosphopantetheine binds in order to connect the incoming extender unit (Walsh et al., 1997. Curr Opin Chem Biol. 1(3):309-15).

ChdQI

The deduced chdQI product is involved in cyclisation/aromatization of the polyketide chain. The ChdQI amino acid sequence is most similar to the CmmQI protein from *S. griseus* subsp. *griseus*, with 33% identity. The cmmQI product codes for a cyclase/aromatase that would participate in the cyclisation and aromatization of the first ring. It also shows similarity to the *S. argillaceus* mithramycin aromatase/cyclase (mtmQI), presumably involved in C-7/C12 first ring closure. It also shows similarity to the otcD1 (also named oxyK by Zhang et al., 2006, J Nat Prod. 69(11):1633-6; Zhang et al., 2007, J Biol Chem. 282(35):25717-25) gene from *S. rimosus*. The otcD1 product was identified as a bifunctional cyclase/aromatase (Petković et al., 1999. J Biol Chem. 274(46):32829-34). and was proved not only to catalyze the correct formation of the D ring, but to also influence the final length of the nascent polyketide chain. A disruption of the otcD1 gene in the oxytetracycline cluster leads to four truncated (by up to 10 carbons) shunt products. Within the ChdQI there are the highly conserved amino acids, which are according to the homologous cyclise/aromatase TcmN, responsible for the determination of the final length of the polyketide and for its proper regiospecific cyclisation and aromatization (Ames et al., 2008, PNAS; 105(14): 5349-5354). These amino acids are at positions Trp-32, Phe-36, Trp-69, Ser-71, Arg-73, Phe-92, Met-95 in Trp-99.

ChdQII

Interestingly, while ChdQI and ChdQII both align with OtcD1(or OxyK)—with 33% and 58% identity, respectively—, there is only 29% identity between the two of them. Interestingly as well is the fact that only chdQII shows a typical didomain architecture with N- and C-terminal halves having a reasonable similarity to each other. ChdQII is a bifunctional cyclase/aromatase that lies next to the ChdT ketoreductase, and is presumably the cyclase that is involved in D ring aromatisation. It has been previously suggested by Petkovic et al. (1999. J Biol Chem. 274(46):32829-34) that there is a mandatory functional relationship between the OtcD1 cyclase/aromatase and the C-9 ketoreductase, since despite the lack of OtcD1, aromatic rings can still be synthesised. Similarly as in the case of ChdQI, there are the highly conserved amino acids at positions Trp-32, Phe-36, Trp-69, Ser-71, Arg-73, Phe-92, Met-95 in Trp-99. These are, according to the homologous cyclise/aromatase TcmN, responsible for the determination of the final length of the polyketide and for its proper regiospecific cyclisation and aromatization, either of the ring B or C (Ames et al., 2008, PNAS; 105(14): 5349-5354).

CdX

The predicted protein is homologous to OxyI and MtmX, both presumably involved in the formation of the final ring A in the biosynthesis of oxytetracycline and mitramycin, respectively (Lombo et al., 1996, Gene. 172(1):87-91; Zhang et al., 2006, J Nat Prod. 69(11):1633-6).

ChdL

The deduced protein product of the chdL gene shows a profound amino acid sequence similarity (53% identity) to an acyl CoA ligase. Similarly to all the ORFs described (or identified) so far, this one also shows a high degree of similarity to one of the genes from the *S. griseus* subsp. *griseus* chromomycin and the *S. argillaceus* mithramycin gene clusters (Lombo et al., 1996. Gene. 172(1):87-91).

ChdMII

In accordance with the chemical structure of chelocardin, there are two methyltransferases within the chelocardin cluster, and both of their functions can be clearly resolved from the translated amino acid BLAST alignment.

The translated amino acid sequence of chdMII is most similar to the C-methyltransferases CmmMII and MtmMII of *S. griseus* subsp. *griseus* (chromomycin) and *S. argillaceus* (mithramycin), respectively (Lozano et al., 2000. J Biol Chem. 275(5):3065-74; Rodriguez et al., 2004, J Biol Chem. February 279(9):8149-58; Abdelfattah and Rohr, 2006. Angew Chem Int Ed Engl. 45(34):5685-9). The two methyltransferases methylate the aromatic C-9. Furthermore, there is no BLASTp identification of any of the genes for oxytetracycline since it does not contain a methyl group at C-9. From these analyses, there is a strong indication that chdMII codes for a methyltransferase that methylates the aromatic C-9 of chelocardin. Similarly as for ChdMI, ChdMII also shows a typical glycine-rich SAM-dependent methyltransferase motif (Y/DXGXGXG [SEQ ID NO: 37]) that interacts with the SAM cofactor, which is used as a source for the methyl group (Martin and McMillan, 2002, Curr. Opin. Struct. Biol.; 12(6): 783-93).

ChdMI

The second methyltransferase within the chelocardin cluster is the C-6 methyltransferase. As expected, ChdL BLAST similarity search returns the OxyF methyltransferase from *S. riniosus* (with 65% identity) which methylates the C-6 of pretetramid in a reaction that yields 6-methyl-pretetramid (Zhang et al., 2006. J Nat Prod. 69(11):1633-6). Moreover, this time there are no hits among any of the chromomycin or mithramycin cluster genes, since they do not have a methyl group at the C-6 position. Therefore, we presume that chdMI codes for C-6 methyltransferase.

ChdN

There is only one amino-group in the chemical structure of chelocardin and chdN is the only ORF that resembles an amidotransferase, according to the aa sequence analysis. It is most similar (52% identity) to the amidotransferase NocG from *Nocardia uniformis* subsp. *tsuyamanensis*, a producer of the monocyclic beta-lactam antibiotic nocardicin A. The second closest hit, with 51% identity, is an aspartate/tyrosine/aromatic aminotransferase from *S. fungicidicus* (enduracidin), followed by aminotransferases from *S. coelicolor* (A3) 2 and many other different *Actinomycetes* species, such as *Frankia* sp. CcI3, *Salinispora tropica*, *Amycolatopsis balhimycina*, *Nonomuraea* sp. ATCC 39727, etc. Although all these amidotransferases belong to a variety of different *actinomycetes*, they all share more than 49% identity with ChdN. Therefore, the gene chdN is an amidotransferase that catalyses the single amidation of chelocardin at the C-4.

ChdT

The protein product of chdT is most similar to oxyJ (*S. rimosus*), followed by simA6 from the simocyclinone gene cluster (*S. antibioticus* Tue6040) and aknA (*S. galilaeus*), all genes coding for ketoreductases. Moreover, the first 60 BLASTp hits return ketoreductases with more than 40% of identity to ChdT, so there is an aromatic PKS ketoreductase involved in the region-specific reduction of the C-9 carbonyl group of the nascent polyketide chain (Hopwood, 1997. Chem. Rev. 97:2465-2497). Two conserved domains can be found within the amino acid sequence of ChdT, namely GXGXXA [SEQ ID NO: 38] and G-3X-G-X-G-3X-A-6X-G [SEQ ID NO: 39], proposed to act as a NADPH-cofactor binding sites (Hopwood and Sherman, 1990, Annual Review of Genetics; 24:37-66; Rawlings and Cronan, 1992, J Biol Chem.; 267(9): 5751-4).

ChdOI

The protein product of chdOI is similar to several monooxygenases, such as oxyE, cmmOI, and mtmOI. They all exhibit significant similarity to flavin adenine dinucleotide (FAD)-dependent monooxygenases involved in the hydroxylation of different polyketides. For OxyE it has been presumed by Zhang et al (1997. Chem. Rev. 97:2465-249). That this FAD-dependent monooxygenase is involved in catalyzing the C-5 oxidation of a 5a,11a-dehydrotetracycline to yield 5a,11a-dehydrooxytetracycline. But since there is a very high degree of similarity (66% identity) between ChdOI and OxyE, and no C-5 oxidation in the chelocardin (or mithramycin or chromomycin), there is a mistake in the current prediction for the function of the OxyE product. According to Abdelfattah and Rohr (2006. Angew Chem Int Ed Engl. 45(34):5685-9), MtmOI is responsible for hydroxylating the C4 of the premithramycinone that eventually becomes the O-atom in the 1'-position of mithramycin. According to the conserved domain search the oxygenase belongs to the family of FAD-dependent monooxygenases, since at the N-terminal end of the protein there is a typical conserved sequence G-X-G-2X-G-3X-A-6X-G ([SEQ ID NO: 40], where X is any amino acid) involved in the FAD-cofactor binding (Mason and Cammack, 1992, Annu. Rev. Microbiol.; 46:277-305).

ChdOII

The product of chdOII is most similar to OxyL, followed by an oxygenase from *S. rochei*, MtmOII from *S. argillaceus* and CmmOII from *S. griseus* subsp. *griseus* oxygenases. The inactivation of mtmOII generated a non-producing mutant strain which generated an unstable compound (Prado et al., 1999. Mol Gen Genet. 261(2):216-25). However, Abdelfattach and Rohr (2006. Angew Chem Int Ed Engl. 45(34):5685-9) provided a vague, indirect proof that the product of MtmOII is responsible for the epoxidation reaction either simultaneously with or shortly after the correct fourth cyclization to give the tetracyclic premithramycin framework, hence hydroxylating the C-12a of the polyketide. In the mithramycin biosynthesis, MtmOII is also involved in controlling the chain length of the growing polyketide as well as the correct region-specificity in the cyclisation step of the fourth ring. ChdOII is according to the conserved domain search also the oxygenase from the family of FAD-dependent monooxygenases, since at the N-terminal end of the protein there is a typical conserved sequence G-X-G-2X-G-3X-A-6X-G ([SEQ ID NO: 41], where X is any aminoacid) involved in the FAD-cofactor binding (Mason and Cammack, 1992, Annu. Rev. Microbiol.; 46:277-305).

ChdOIII

ChdOIII is a very short protein that shows similarity to oxygenase OxyG (*S. rimosus*), a small (11-kDa) quinine-forming oxygenase, possibly involved in the quinine formation of ring A in 4-keto-ATC. According to the conserved domain search, the ChdOIII is an ABM (Antibiotic Biosynthesis Monooxygenase) that does not contain an FAD binding site, neither are there any other prostetic groups, metal ions or cofactors needed for the molecular oxygen activaton.

ChdA

The product of the chdA gene is according to BLASTp most similar to a transcriptional regulator, namely the tetracycline repressor from the TetR family of proteins that are involved in the transcriptional control of multidrug efflux pumps, pathways for the biosynthesis of antibiotics, differentiation processes, etc. Since proteins of the TetR family have been found in 115 genera of gram-positive, alpha-, β-, and gamma-proteobacteria, cyanobacteria, and archaea (Ramos et al., 2005) it is not suprising that the BLAST hits return species from several genera, including the *Burkholderia, Salmonella, Klebsiella, Escherichia, Aeromonas*, etc.

ChdR

The ChdR protein codes for a multidrug efflux resistance protein from the EmrB/QacA subfamily. With 39% identity and 58% similarity it is most similar to the EmrB/QacA of *Frankia alni*, followed by *Nocardia farcinica* (with 35% identity, 55% similarity), and *Salinispora arenicola* (36% identity, 58% similarity). Since chelocardin's mechanism of action is supposedly different from the classical binding of tetracyclines to the 30S ribosomal subunit (Chopra I. 2004. Antimicrob Agents Chemother; 38(4):637-40), the mere presence of an efflux protein without the additional ribosomal protection mechanism should suffice the resistance requirements of the strain.

Within the chelocardin cluster (FIG. 4), two redundant genes are also present. The genes chdGIV and chdTn, coding for a glycosyltransferase and a transposase, respectively, could be an evolutionary remain of the horizontally transferred DNA fragment from a gene cluster of a glycosylated polyketide, such as chromomycin or mithramycin. The chdGIV gene product is most similar to the CmmGIV and MtmGIV glycosyltransferases of the chromomycin (*Streptonzyces griseus* subsp. *griseus*) and mithramycin (*Streptomyces argillaceus*) producers. It is therefore also possible that *A. sulphurea* has a potential to produce glycosylated chelocardin analogues. However, to our knowledge, this has not yet been confirmed in the literature.

Example 10

Heterologous Expression

Heterologous Hosts

A method for the heterologous expression of chelocardin in a substitute *Actinomyces* host is provided. The cloned genes for the biosynthesis of chelocardin have been expressed in heterologous hosts such as *S. lividans* TK24, *S. rimosus* 15883S, *S. albus* G148, and *S. coelicolor* A3(2), *Anzycolatopsis orientalis* and *Nocardia* sp.

Culturing Conditions

Culture conditions were optimized for the expression of the chelocardin biosynthetic gene cluster. The following vegetative medium was used for inoculum preparation: 3 g soy flour, 0.2 g yeast extract, 1.5 mL glucose (50%), 1 g NaCl, 0.2 g CaCO3, tap water up to 200 mL. The inoculum was grown for 24 hours at 30° C. on a rotary shaker at 220 rpm. The following medium was used for production: 40 g soy flour, 10 g yeast extract, 4 g CaCO3, 1 g citric acid, 5 mL glucose (50%), tap water up to 1800 mL. The pH of the production medium was corrected to 7.0. For fermentation, 50 mL of production medium was inoculated with 5% inoculum in a 500 mL Erlenmayer flask and grown at 30° C. on a rotary shaker at 220 rpm for 7 days.

Extracting the Produced Chelocardin 50 mL of fermentation broth was acidified to pH 1-2 with HCl, saturated with NaCl, followed by two extractions with 25 mL of butanol. The extracts were vacuum-dried and subsequently resuspended in methanol to the desired concentration.

HPLC Analysis of the Product

A reverse gradient HPLC method was devised that makes use of two standard mobile phases:

Mobile phase A (pH 2.75): 100 mL HPLC-grade acetonitrile, 10 mL of 1 M ammonium acetate solution and 1 mL of TFA were mixed in a total volume of 1 L, using HPLC-grade water.

Mobile phase B (pH 2.7): 100 mL HPLC-grade water, 10 mL of 1 M ammonium acetate and 1 mL of TFA were mixed in a total volume of 1 L, using HPLC-grade acetonitrile.

HPLC analysis was run on a 150 mm×4.6 mm Thermo-Hypersil C18-BDS reverse phase column with a silica particle size of 3 μm that has an in line short guard cartridge containing the same silica as the column but with a silica particle size of 5 μm. The generic HPLC gradient details are shown below:

Flow rate: 1 ml/min
Column oven temperature: 30° C.
UV wave-length analysis: 279 nm
Gradient conditions: T=0 min, 10% B; T=1 min, 10% B; T=25 min, 95% B; T=29 min, 95% B; T=29.5 min, 10% B; T=36 min, 10% B.

Bioassay on the Model Organism Micrococcus luteus and Escherichia coli

The 0.5 mL HPLC fractions were collected every 30 seconds. Qualitative agar diffusion bioassay of the fractions was performed on petri dishes containing *Micrococcus luteus* and *Escherichia coli* as test strains. Sterile disks were impregnated with 20 μL of the collected fractions and incubated on the seeded 2TY agar for 24 hours at 37° C. The fractions that showed zones of inhibition were subjected to further NMR/MS analysis.

MS Analysis of the Product

An HPLC method was carried out to collect fractions of the extracts from cultures of heterologous expression hosts carrying the entire gene cluster encoding for chelocardin biosynthesis. Biological activities of the fractions were tested against *Micrococcus luteus*. The active fractions were subjected to further LC-MS/MS analysis which confirmed the presence of a molecule of m/z=412 that corresponds to a chelocardin molecule with a proton adduct. For the LC-MS/MS analyses, the Agilent 1100 series coupled with Watters Micromass Quattro micro detector were used together with the Gemini 3μ C18 110A (150×2.1 mm (Phenomenex, USA) column were used under the following running conditions:

Column temperature: 45° C.; Mobile phase A=0.05% trifluoroacetic acid—MilliQ water, B=acetonitrile; Flow: 0.24 ml/min; Gradient:

| time (min) | A (%) | B (%) |
| --- | --- | --- |
| 0 | 80 | 20 |
| 13 | 10 | 90 |
| 15 | 10 | 90 |
| 15.1 | 80 | 20 |
| 20 | 80 | 20 |

Injection volume: 10 μL of sample
Detector conditions:
Ionisation: ESI+
Method: SIR
Dwell time: 0.1 s; Cone 20 V; Capillary 3.0 kV; Extractor: 3 V; Source temperature: 120° C.; Desolvation temperature: 350° C.; Cone gas flow: 30 L/h; Desolvation gas flow: 500 L/h; Multiplier: 650 V.

Example 11

Generation of C9-Demethyl Chelocardin Analogue

An in-frame chdMII gene inactivation experiment is performed, eliminating any possible polar effects on chdQI. Two PCR products (chdMIIa and chdMIIb) flanking the 402 nt (134 aa) sequence of chdMII are amplified using the primers (with restriction sites underlined):

```
                                        [SEQ ID NO: 42]
chdMIIa-forward:
5'-GAATTCCCACCGTCCACATAGGAAAG-3' (EcoRI
restriction site),

[SEQ ID NO: 43]
chdMIIa-reverse:
5'-GACGTCGTGATGATCACCAATGTGCTGC (ZraI restriction
site),

[SEQ ID NO: 44]
chdMIIb-forward:
5'-GGCGCCCAGCTTCAACGACGGC-3' (SfoI restriction
site),

[SEQ ID NO: 45]
chdMIIb-reverse:
5'-GAATTCCGACCTCAGCGTCCACATC-3' (EcoRI restriction
site).
```

The 1802 and 1282 bp products of chdMIIa and chdMIIb, respectively, are separately cloned into the SmaI linearized and dephosphorylated pUC19 and confirmed by sequencing. The EcoRI-ZraI chdMIIa and SfoI-EcoRI chdMIIb products are cloned simultaneously into the EcoRI linearized and dephosphorylated pIJ4026, creating the pIJ4026-chdMII402. The proper orientation of the both inserts is assured by the one-side blunt ends produced by the ZraI and SfoI restriction enzymes. The unaltered reading frame is confirmed after sequencing using the VectorNTI software. The plasmid pIJ4026-chdMII402 is inserted into the *A. sulphurea* chromosome by a single cross-over homologous recombination, and transformants were selected using erythromycin (50 μg/mL). Colonies that underwent a second crossover, hence shortening the wild type chdMII gene by 402 nt (134 aa), are chosen on the basis of the erythromycin-sensitive phenotype. The mutants with the truncated chdMII are confirmed by southern hybridisation using the chdMII gene as a probe. The chromosomal DNAs of the wild type *A. sulphurea* and the ΔchdMII mutants are digested with EcoRI. The ΔchdMII strains show a single hybridization signal at the expected 8,696 kbp in comparison with the two bands (of 7,580 and 1,518 kbp) of the wild type. Fermentation of the mutant strains, product extraction and the MS analysis are performed as described in the Example 10. The resulting molecule is a chelocardin with R7=H.

1) Position: R1: NH2 (otc homologue of OxyD (Zhang et. al., 2006, Appl. Environ. Microbiol., 72(4):2573-2580)

In this case, we would express oxyD gene from oxytetracycline gene cluster together with entire gene cluster encoding chelocardin biosynthesis.

Example 12

Generation of Amide-Derived Chelocardin Analogs

Structure 1

To generate the amide-derived chelocardin analogue at the position R1, the intact oxyD gene (GenBank nucleotide sequence DQ143963, nucleotides from 3686 to 5524; Zhang et al., 2006, Appl. Environm. Microbiol.; 72(4):2573-2580) that is involved in the malonamyl-CoA starter unit biosynthesis of the OTC was cloned into the phiC31/phiBT1/pSAM-based integrative vector and/or replicative vector under the act/erm/erm* promoter. After the transformation of the vectors, fermentation of the productive strains, product extraction and the MS analysis were performed as described above. The following structure is obtained:

Structure 1

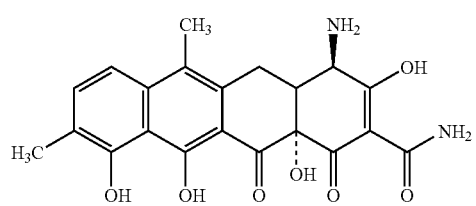

Structure 2

Position: R2: —OH (inactivation of chdN (Zhang et. al., 2006, Appl. Environ. Microbiol., 72(4):2573-2580))

The inactivation of the chdN gene encoding C4-aminotransferase from chelocardin cluster should, according to the prior art, result in the presence of an OH-group at position C4.

Structure 2

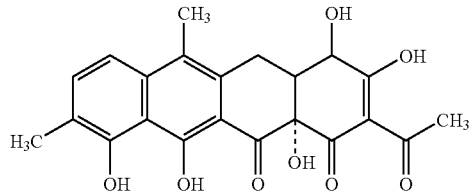

Structure 3

Position: R2: N(CH3)2 (co-expression with OxyT (Zhang et. al., 2006, Appl. Environ. Microbiol., 72(4):2573-2580)). In this case, we would express oxyT methyltransferase gene from oxytetracycline gene cluster together with entire gene cluster encoding chelocardin biosynthesis.

Structure 3

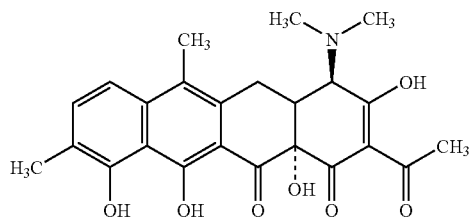

Structure 4

Position: R3: OH (otc co-expression OxyE and/or OxyL and/or OxyS and/or OxyG (Zhang et. al., 2006, Appl. Environ. Microbiol., 72(4):2573-2580), and Theriault et al., 1982, J. Antibiot March; 35(3):364-6.) In this case, we would express oxyE (or oxyL, or oxyS or oxyG) hydroxylase gene from oxytetracycline gene cluster together with entire gene cluster encoding chelocardin biosynthesis.

Structure 4

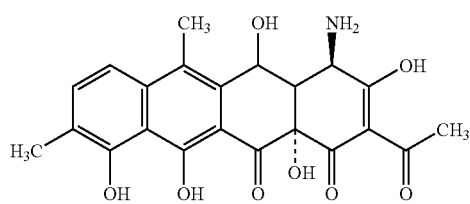

Structure 5

Position: R4: CH3 and OH (co-expression with OxyS (OtcC) (Peric-Concha et al., 2005, J. Biol. Chem.; 280(45): 37455-60), and Theriault et al., 1982, J. Antibiot March; 35(3):364-6) or OxyE, or OxyL, or oxyG (Zhang et al., 2006, Appl. Environ. Microbiol., 72(4):2573-2580). In this case, we would express oxyS (otcC) or oxyE, or oxyL, or oxyG hydroxylase gene from oxytetracycline gene cluster together with entire gene cluster encoding chelocardin biosynthesis.

The stereochemistry of NH₂ in the opposite epimeric form has been described by (Theriault, 1982, J Antibiot.; 35(3): 364-6). The epimeric form of Structure 5 is previously unknown.

Structure 5

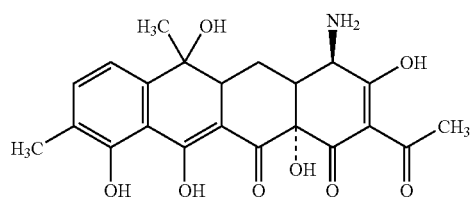

Structure 6

Position R4: H (inactivation of chdMI). (Zhang et. al., 2006, Appl. Environ. Microbiol., 72(4):2573-2580) The inactivation of the chdMI gene encoding C6 methyltransferase from chelocardine cluster should, according to the available literature and our own results, result in the absence of a CH3-group at position C6.

Structure 6

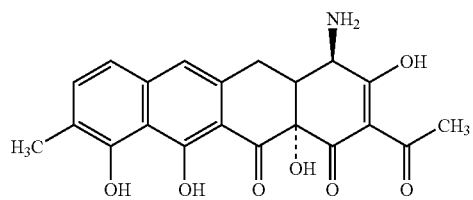

Structure 7

Position R5: Cl (co-expression with chl (cts4) (Dairi et al, 1995, Biosci. Biotechnol. Biochem. 59(6):1099-106))

In this case, we would express chl gene catalysing chlorination at the position C7 from chlortetracycline gene cluster together with entire gene cluster encoding chelocardin biosynthesis.

Structure 7

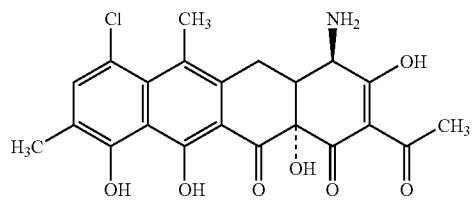

Structure 8

Position R7: H (inactivation of chdMII)

The inactivation of the chdMII gene encoding C9 methyltransferase from chelocardin cluster should, according to the available literature data and our own results, result in the absence of a CH3-group at position C6.

Structure 8

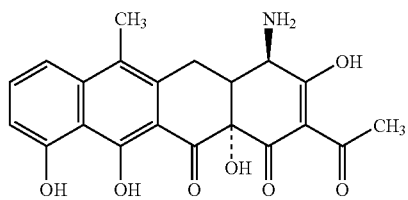

Structure 9

Position OR: OCH3 (co-expression with tcmO (Summers et al., 1992, J. Bac.; 174:(6):1810-1820)

In this case, we would express tcmO gene from tetracenomycin gene cluster together with entire gene cluster encoding chelocardin biosynthesis.

Structure 9

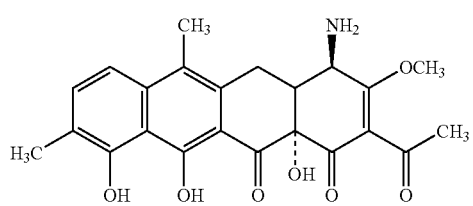

The position of double bonds which would be altered after proposed modifications at carbons C4, C5 and C6 could not be defined precisely at this point due to possible spontaneous chemical rearrangement and/or possible tautomeric forms/isomers which can also influence the oxidative states of hydroxyl and keto groups at carbons 10, 11, 12 and carbon 1.

Structure 10

Using the minimum set of enzymes of the invention, the following tetracycline structure is obtained:

Structure 10

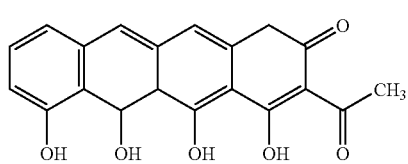

Example 13

Identification of Homologues

Using bioinformatic tools, the following homologues of genes of the invention were identified. Homologues shown in Table 3 can substitute the original genes/sequences in methods of the invention. The "% identity" is also given, as calculated with NCBI/BLAST algorithms (blastp and blastx). The BLAST search was performed against a non-redundant protein sequences database with the default general and scoring parameters (Altschul et al., 1990, *J Mol Biol,* 215, 403-10).

TABLE 2

| gene | homologue | strain | % identity |
|---|---|---|---|
| chdP | OxyA | S. rimosus | 77 |
| chdK | OxyB | S. rimosus | 73 |
| chdS | OxyC | S. rimosus | 59 |
| chdQI | cyclase-like protein | Streptomyces sp. WP 4669 | 33 |
| chdMII | C9-methyltransferase | S. griseus subsp. griseus | 44 |
| chdN | aminotransferase | Frankia sp | 51 |
| chdOI | OxyE-oxygenase | S. rimosus | 64 |
| chdMI | OxyF-C6 methyltransferase | S. rimosus | 65 |
| chdOIII | OxyG-oxygenase | S. rimosus | 58 |
| chdL | acyl-CoA ligase | S. griseus subsp. griseus | 54 |
| chdX | OxyI-cyclase | S. rimosus | 63 |
| chdT | OxyJ-ketoreductase | S. rimosus | 74 |
| chdQII | OxyK-cyclase | S. rimosus | 58 |
| chdOII | OxyL-oxygenase | S. rimosus | 56 |

The invention claimed is:

1. A genetically engineered cell of the order of Actinomycetales,
   said cell being capable of producing a tetracycline compound,
   said tetracycline compound being produced by said cell by a genetically engineered biosynthetic pathway, wherein
   said genetically engineered biosynthetic pathway of said cell includes all polypeptides of SEQ ID NO: 1-5 and 8, wherein
   each of said polypeptides of SEQ ID NO: 1-5 and 8 can be substituted by a substituting polypeptide which is at least 95% identical to said substituted polypeptide, and wherein said substituting polypeptide has the same catalytic function as said substituted polypeptide.

2. A cell of claim 1, wherein said genetically engineered biosynthetic pathway of said cell comprises a reaction catalysed by a further polypeptide selected from the group consisting of SEQ ID NO: 9 to 18, wherein said further polypeptide of SEQ ID NO: 9, 10 or 13 can be substituted by a substituting polypeptide which is at least 95% identical to said substituted further polypeptide, and wherein said substituting polypeptide has the same catalytic function as said substituted further polypeptide.

3. A gene cluster encoding a tetracycline biosynthetic pathway, said gene cluster comprising nucleic acid coding for all polypeptides of SEQ ID NO: 1-5 and 8, wherein
   each one of said polypeptides of SEQ ID NO: 1-5 and 8 can be substituted by a substituting polypeptide which is at least 95% identical to said substituted polypeptide, wherein said substituting polypeptide has the same catalytic function as said substituted polypeptide.

4. A gene cluster of claim 3, said gene cluster comprising a nucleic acid coding for a further polypeptide selected from the group consisting of SEQ ID NO: 9 to 18, wherein
   said further polypeptide SEQ ID NO: 9, 10 or 13 can be substituted by a substituting polypeptide which is at least 95% identical to said substituted further polypeptide, and wherein said substituting polypeptide has the same catalytic function as said substituted further polypeptide.

5. Method for the biosynthetic production of a tetracycline compound,
   said method comprising the steps of
   providing the cell of claim 1,
   providing a substrate,
   incubating said substrate with said cell under permissible conditions, and
   obtaining said tetracycline compound.

* * * * *